US009796971B2

(12) United States Patent
Ciplys et al.

(10) Patent No.: US 9,796,971 B2
(45) Date of Patent: Oct. 24, 2017

(54) GENERATION OF NATIVE RECOMBINANT SECRETED HUMAN ENDOPLASMIC RETICULUM CHAPERONES BY USING THEIR NATIVE SIGNAL SEQUENCES IN YEAST EXPRESSION SYSTEMS

(71) Applicant: UAB BALTYMAS, Vilnius (LT)

(72) Inventors: Evaldas Ciplys, Vilnius (LT); Rimantas Slibinskas, Vilnius (LT); Kestutis Sasnauskas, Vilnius (LT); Marek Michalak, Edmonton (CA); Leslie Ina Gold, Darien, CT (US)

(73) Assignee: UAB BALTYMAS, Vilnius (LT)

( * ) Notice: Subject to any disclaimer, the term of this patent is extended or adjusted under 35 U.S.C. 154(b) by 0 days.

(21) Appl. No.: 14/594,485

(22) Filed: Jan. 12, 2015

(65) Prior Publication Data

US 2015/0191713 A1 Jul. 9, 2015

Related U.S. Application Data

(63) Continuation of application No. PCT/US2013/049843, filed on Jul. 10, 2013.

(60) Provisional application No. 61/670,768, filed on Jul. 12, 2012.

(51) Int. Cl.
| | |
|---|---|
| *C12N 9/90* | (2006.01) |
| *C07K 14/47* | (2006.01) |
| *C12N 15/81* | (2006.01) |
| *C12P 21/02* | (2006.01) |

(52) U.S. Cl.
CPC .............. *C12N 9/90* (2013.01); *C07K 14/47* (2013.01); *C07K 14/4702* (2013.01); *C07K 14/4728* (2013.01); *C12N 15/81* (2013.01); *C12P 21/02* (2013.01); *C12Y 503/04001* (2013.01)

(58) Field of Classification Search
None
See application file for complete search history.

(56) References Cited

U.S. PATENT DOCUMENTS

| | | | |
|---|---|---|---|
| 5,330,901 A * | 7/1994 | Prevatt ................ | C07K 14/765 435/254.23 |
| 2008/0118950 A1* | 5/2008 | Gellissen ............... | C07K 14/47 435/69.1 |
| 2010/0145016 A1* | 6/2010 | Michalak ............... | C12P 21/02 530/350 |
| 2011/0014651 A1 | 1/2011 | Chiba et al. | |
| 2011/0143396 A1 | 6/2011 | Choi | |
| 2012/0121630 A1* | 5/2012 | Bryan .................. | A61K 39/245 424/186.1 |

OTHER PUBLICATIONS

Corbett et al., J Biol Chem. Sep. 1, 2000;275(35):27177-85.The conformation of calreticulin is influenced by the endoplasmic reticulum luminal environment.*
Ciplys et al., Yeast, (Sep. 2015) vol. 32, Supp. Suppl. 1, pp. S245-S246. Abstract Number: PS15-2.Meeting Info: 27th International Conference on Yeast Genetics and Molecular Biology. Trento, Italy. Sep. 6, 2015-Sep. 12, 2015.*
GenBank: AD000092.1*Homo sapiens* DNA from chromosome 19p13.2 cosmids R31240, R30272 and R28549 containing the EKLF, GCDH, CRTC, and RAD23A genes, genomic sequence dowloaded on Aug. 3, 2016.*
Sleep et al The secretion of human serum albumin from the yeast *Saccharomyces cerevisiae* using five different leader sequences1990, Bio/Technology, pp. 42-46).*
Ahmad et al., Appl Microbiol Biotechnol (2014) 98:5301-5317; MINI-REVIEWProtein expression in Pichia pastoris: recent achievements and perspectives for heterologous protein production.*
Cereghino et al., FEMS Microbiology Reviews 24 (2000) 45-66 Heterologous protein expression in the methylotrophic yeast Pichia pastoris.*
Pichia Expression Kit User Guide, Invitrogen, Life Techonolgies, downloaded 2016; pp. 1-97.*
Idiris et al., Engineering of protein secretion in yeast: strategies and impact on protein production Appl Microbiol Biotechnol (2010) 86:403-417.*
Brodsky et al., Protein folding and quality control in the endoplasmic reticulum: Recent lessons from yeast and mammalian cell systems Current Opinion in Cell Biology 2011, 23:464-475.*
Hahm et al Refolding and Purification of Yeast Carboxypeptidase Y Expressed as Inclusion Bodies in *Escherichia coli* Protein Expression and Purification 22, 101-107 (2001).*
Kincaid et al., Misfolded Proteins Traffic from the EndoplasmicReticulum (ER) Due to ER Export Signals Molecular Biology of the Cell vol. 18, 455-463, Feb. 2007.*
çelik et al., Research review paper Production of recombinant proteins by yeast cells Biotechnology Advances 30 (2012) 1108-1118.*
Antoniou, A. N., et al., "The oxidoreductase ERp57 efficiently reduces partially folded in preference to fully folded MHC class I molecules," The EMBO Journal 2002;21(11):2655-2663.
Apte-Deshpande, A., et al., "Efficient expression and secretion of recombinant human growth hormone in the methylotrophic yeast Pichia pastoris: potential applications for other proteins," Biotechnol. Appl. Biochem. 2009;54:197-205.
Carlino, A., et al., "Interactions of liver Grp78 and *Escherichia coli* recombinant Grp78 with ATP: Multiple species and disaggregation," Proc. Natl. Acad. Sci. USA 1992;89:2081-2085.
Celli, C. M., et al., "Role of GRP58 in Mitomycin C-induced DNA Cross-Linking," Cancer Res. 2003;63:6016-6025.

(Continued)

*Primary Examiner* — Maria Leavitt
(74) *Attorney, Agent, or Firm* — Shelly Guest Cermak; Cermak Nakajima & McGowan LLP

(57) ABSTRACT

A method using yeast as a host for production of human ER chaperone proteins, using endogenous signal peptides of intracellular human proteins that are recognized and correctly processed in the yeast cells to subsequently lead to the secretion of the human proteins. The resultant proteins possessed native amino acid sequence and were biologically active. Moreover, secretion allowed simple one-step purification of native recombinant human proteins with high yields.

10 Claims, 24 Drawing Sheets

(56) References Cited

OTHER PUBLICATIONS

Cereghino, J. L., et al., "Heterologous protein expression in the methylotrophic yeast Pichia pastoris," FEMS Microbiol. Rev. 2000;24:45-66.

Dana, R. C., et al., "Heat shock proteins bind calcitonin," Endocrinol. 1990;126(1):672-674.

Frickel, E.-M., et al., "ERp57 Is a Multifunctional Thiol-Disulfide Oxidoreductase," J. Biol. Chem. 2004;279 (18):18277-18287.

Ghosalkar, A., et al., "Secretory expression of interferon-alpha 2b in recombinant Pichia pastoris using three different secretion signals," Protein Expression and Purification 2008;60:103-109.

Gold, L. I., et al., "Calreticulin: non-endoplasmic reticulum functions in physiology and disease," The FASEB Journal 2010;24:665-683.

Greives, M. R., et al., "Exogenous calreticulum improves diabetic wound healing," Wound Rep. Reg. 2012;20:715-730.

Hirano, N., et al., "Molecular cloning of the human glucose-regulated protein ERp57/GRP58, a thiol-dependent reductase," Eur. J. Biochem. 1995;234:336-342.

Ji, H., et al., "A two-dimensional gel database of human colon carcinoma proteins," Electrophoresis 1997;18:605-613.

Krause, K.-H., et al., "Sequence similarity of calreticulin with a Ca2+-binding protein that co-purifies with an Ins (1,4,5)P3-sensitive Ca2+ store in HL-60 cells," Biochem. J. 1990;270:545-548.

Nanney, L. B., et al., "Calreticulin Enhances Porcine Wound Repair by Diverse Biological Effects," Am. J. Pathol. 2008;173(3):610-630.

Okabayashi, K., et al., "Secretory Expression of the Human Serum Albumin Gene in the Yeast Saccharomyces cerevisiae," J. Biochem. 1991;110:103-110.

Thim, L., et al., "Secretion and processing of insulin precursors in yeast," Proc. Natl. Acad. Sci. USA 1986;83:6766-6770.

UniProtKB—P07237 (PDIA1_HUMAN), Mar. 14, 2016, http://www.uniprot.org/uniprot/P07237, pp. 1-6.

Hale, W. G., et al., Collins Dictionary of Biology, Second Ed., 1995, HarperCollins Publishers, Glasgow, Scotland, pp. 366-367 and 566-567.

Choo, K. H., et al., "Flanking signal and mature peptide residues influence signal peptide cleavage," BMC Bioinformatics 2008;9(Suppl. 12):S15, 11 pages.

Abcam product: GRP78 BiP protein (Active) (ab78432), 2012, http://www.abcam.com/GRP78-BiP-protein-Active-ab78432.html.

Abcam product: Calreticulin protein (Human) (ab91577), 2012, http://www.abcam.com/Calreticulin-protein-Human-ab91577.html.

Abcam product: ERp57 protein (His tag) (ab92937), 2012, http://www.abcam.com/ERp57-protein-His-tag-ab92937.html.

Andrin, C., et al., "Expression and purification of mammalian calreticulin in Pichia pastoris," Protein Expr. Purif. 2000;20(2):207-215.

Baksh, S., et al., "Expression and purification of recombinant and native calreticulin," Protein Expr. Purif. 1992;3(4):322-331.

Bedard, K., et al., "Cellular functions of endoplasmic reticulum chaperones calreticulin, calnexin, and ERp57," Int. Rev. Cytol. 2005;245:91-121.

Benyair, R., et al., "Protein quality control, retention, and degradation at the endoplasmic reticulum," Int. Rev. Cell Mol. Biol. 2011;292:197-280.

Braakman, I., et al., "Protein folding and modification in the mammalian endoplasmic reticulum," Annu. Rev. Biochem. 2011;80:71-99.

Braakman, I., et al., "Folding of viral envelope glycoproteins in the endoplasmic reticulum," Traffic 2000;1(7):533-539.

Capitani, M., et al., "The KDEL receptor: new functions for an old protein," FEBS Lett. 2009;583:3863-3871.

Chakrabati, A., et al., "A review of the mammalian unfolded protein response," Biotechnol. Bioeng. 2011;108 (12):2777-2793.

Chaput, N., et al., "Molecular determinants of immunogenic cell death: surface exposure of calreticulin makes the difference," J. Mol. Med. (Berl) 2007;85(10):1069-1076.

Choo, K. H., et al., "Flanking signal and mature peptide residues influence signal peptide cleavage," BMC Bioinformatics 2008;9(Suppl. 12):S15.

Ciplys, E., et al., "Overexpression of human calnexin in yeast improves measles surface glycoprotein solubility," FEMS Yeast Research 2011;11:514-523.

Ciplys, E., et al., "Saccharomyces cerevisiae—a perfect host for expression and simple one-step purification of active tag-gree human BiP/GRP78 protein," FEBS J. 2012;279(1):344-345.

Ciplys, E., et al., "Native signal peptide of human ERp57 disulfide isomerase mediates secretion of active native recombinant ERp57 protein in yeast Saccharomyces cerevisiae," Protein Exp. Purif. 2013;89(2):131-135.

Ciplys, E., et al., "Generation of human ER chaperone BiP in yeast Saccharomyces cerevisiae," Microbial Cell Factories 2014;13(1):22.

Ciplys, E., et al., "High level secretion of native recombinant human calreticulin in yeast," Microbial Cell Factories 2015;14(1):22.

Corrigall, V. M., et al., "The Human Endoplasmic Reticulum Molecular Chaperone BiP Is an Autoantigen for Rheumatoid Arththritis and Prevents the Induction of Experimental Arthritis," J. Immunol. 2001;166(3):1492-1498.

Damasceno, L. M., et al., "Protein secretion in Pichia pastoris and advances in protein production," Appl. Microbiol. Biotechnol. 2012;93:31-39.

Gonzalez-Gronow, M., et al., "GRP78: A Multifunctional Receptor on the Cell Surface," Antioxid. Redix. Signal. 2009;11(9):2299-2306.

Groenendyk, J., et al., "Biology of Endoplasmic Reticulum Stress in the Heart," Circ. Res. 2010;107(10):1185-1197.

Hamilton, S. R., et al., "Glycosylation engineering in yeast: the advent of fully humanized yeast," Curr. Op. Biotechnol. 2007;18:387-392.

Hebert, D. N., et al., "Calnexin, calreticulin, and BiP/Kar2p in protein folding," Cold Spring Harbor Symposia on Quantitative Biology 1995;60:405-415.

Hetz, C., et al., "The Disulfide Isomerase Grp58 Is a Protective Factor against Prion Neurotoxicity," J. Neurosci. 2005;25(11):2793-2802.

High, S., et al., "Glycoprotein folding in the endoplasmic reticulum: a tale of three chaperones?" FEBS Lett. 2000;476:38-41.

Hou, J., et al., "Metabolic engineering of recombinant protein secretion by Saccharomyces cerevisiae," FEMS Yeast Res. Apr. 25, 2012, doi: 10.111/j.1567-1364.2012.00810.x[epub ahead of print].

Houen, G., et al., "Human Placental Calreticulin: Purification, Characterization and Association with other Proteins," Acta Chemica Scandinavica 1994;48:905-911.

Lee, A. S., et al., "GRP78 Induction in Cancer: Therapeutic and Prognostic Implications," Cancer Res. 2007;67:3496-3499.

Li, J., et al., "Stress Induction of GRP78/BiP and Its Role in Cancer," Curr. Mol. Med. 2006;6:45-54.

Luo, B., et al. "The critical roles of endoplasmic reticulum chaperones and unfolded protein response in tumorigenesis and anticancer therapies," Oncogene, Apr. 16, 2012; doi: 10.1038/onc.2012.130 [Epub ahead of print].

Luz, J. M., et al., "Expression and secretion of human protein disulphide isomerase in Saccharomyces cerevisiae," Biochem. Soc. Transactions 1994;22(1):76S.

Ma, Y., et al., "ER chaperone functions during normal and stress conditions," J. Chem. Neuroanat. 2004;28:51-65.

Maffei, A., et al., "MHC Class I Antigen Processing Pathways," Human Immunol. 1997;54:91-103.

Malhotra, J. D., et al., "The endoplasmic reticulum and the unfolded protein response," Seminars in Cell & Developmental Biology 2007;18:716-731.

Mattanovich, D., et al., Methods Mol. Biol. 2012;824:329-358.

Morito, D., et al., "ER stress proteins in autoimmune and inflammatory diseases," Front Immunol. 2012;3(48):1-8.

Ni M., et al., "Beyond the endoplasmic reticulum: atypical GRP78 in cell viability, signalling and therapeutic targeting,". Biochem. J. 2011;434:181-188.

(56) References Cited

OTHER PUBLICATIONS

Nicchitta, C. V., et al., "The immunological properties of endoplasmic reticulum chaperones: a conflict of interest?" Essays in Biochem. 2000;36:15-25.

Obeid, M., et al., "Calreticulin exposure dictates the immunogenicity of cancer cell death," Nature Med. 2007;13(1):54-61.

Panayi, G. S., et al., "BiP regulates autoimmune inflammation and tissue damage," Autoimmun. Rev. 2006;5:140-142.

Peters, L. R., et al., "Endoplasmic Reticulum Calcium Depletion Impacts Chaperone Secretion, Innate Immunity, and Phagocytic Uptake of Cells," J. Immunol. 2011;187:919-931.

Rokeach, L. A., et al., "High-level bacterial expression, purification and characterization of human calreticulin," Protein Eng. 1991;4(8):981-987.

Silvennoinen, L., et al., "Identification and Characterization of Structural Domains of Human ERp57," J. Biol. Chem. 2004;279(14):13607-13615.

Spear, E., et al., "The Unfolded Protein Response: No Longer Just a Special Teams Player," Traffic 2001;2:515-523.

StressMarq product: GRP78 (Recombinant, Human, Native sequence), (SP-119B). 2012. http://www.stressmarq.com/Products/Proteins/SPR-119B.aspx.

Turano, C., et al., "ERp57/GRP58: A Protein With Multiple Functions," Cell. Mol. Biol. Lett. 2011;16:539-563.

USBiological Product: Recombinant human BIP protein (B1770-01). 2012. https://www.usbio.net/molecular-biology/B1770-1.

USBiological Product: Recombinant human Calreticulin (C1036-02L1). 2012. https://www.usbio.net/molecular-biology/C1036-02L1.

USBiological Product: Recombinant human PDIA3 protein (E2291-75E). 2012. https://www.usbio.net/molecular-biology/E2291-75E.

Wearsch, P. A., et al., "The quality control of MHC class I peptide loading," Curr. Op. Cell Biol. 2008;20:624-631.

Wemeau, M., et al., "Calreticulin exposure on malignant blasts predicts a cellular anticancer immune response in patents with acute myeloid leukemia," Cell Death and Disease 2010;1:e104.

Xiong, R., et al., "Secreted expression of human lysozome in the yeast *Pichia pastoris* under the direction of the signal peptide from human serum albumin," Biotechnol. Appl. Biochem. 2008;51:129-134.

Yoo, S.-A., et al., "A novel pathogenic role of the ER chaperone GRP78/BiP in rheumatoid arthritis," J. Exp. Med. 2012;209(4):871-886.

Zhang, J.-X., et al. "Quality Control in the Secretory Pathway: The Role of Calreticulin, Calnexin and BiP in the Retention of Glycoproteins with C-Terminal Truncations," Mol. Biol. Cell 1997;8:1943-1954.

Zhang, Y., et al., "Assembly of MHC Class I Molecules within the Endoplasmic Reticulum," Immunol. Res. 2006;34(1-2):151-162.

Zimmermann, R., et al., "Protein translocation across the ER membrane," Biochimica et Biophysica Acta 2011;1808:912-924.

Extended European Search Report for European Patent App. No. 13816756.4 (Feb. 24, 2016).

International Search Report for PCT Patent App. No. PCT/US2013/049843 (Nov. 22, 2013).

Signal peptide from Wikipedia, https://en.wikipedia.org/wiki/Signal_peptide, downloaded Mar. 14, 2016.

UniProtKB—P27797 (CALR_HUMAN), http://www.uniprot.org/uniprot/P27797, downloaded Mar. 14, 2016.

UniProtKB—P07237 (PDIA1_HUMAN), http:www.uniprot.org/uniprot/P07237, downloaded Mar. 14, 2016.

Afshar, N., et al., "Retrotranslocation of the Chaperone Calreticulin from the Endoplasmic Reticulum Lumen to the Cytosol," Mol. Cell. Biol. 2005;25(20):8844-8853.

Højrup, P., et al., "Human placental calreticulin," Eur. J. Biochem. 2001;268:2558-2565.

Michalak, M., et al., "Calreticulin: one protein, one gene, many functions," Biochem. J. 1999;344:281-292.

Michalak, M., et al., "Calreticulin, a multi-process calcium-buffering chaperone of the endoplasmic reticulum," Biochem. J. 2009;417:651-666.

* cited by examiner

FIGURE 5

```
  1 MKLSLVAAML LLLSAARAEE EDKKEDVGTV VGIDLGTTYS CVGVFKNGRV

51 EIIANDQGNR ITPSYVAFTP EGERLIGDAA KNQLTSNPEN TVFDAKRLIG

101 RTWNDPSVQQ DIKFLPFKVV EKKTKPYIQV DIGGGQTKTF APEEISAMVL

151 TKMKETAEAY LGKKVTHAVV TVPAYFNDAQ RQATKDAGTI AGLNVMRIIN

201 EPTAAAIAYG LDKREGEKNI LVFDLGGGTF DVSLLTIDNG VFEVVATNGD

251 THLGGEDFDQ RVMEHFIKLY KKKTGKDVRK DNRAVQKLRR EVEKAKRALS

301 SQHQARIEIE SFYEGEDFSE TLTRAKFEEL NMDLFRSTMK PVQKVLEDSD

351 LKKSDIDEIV LVGGSTRIPK IQQLVKEFFN GKEPSRGINP DEAVAYGAAV

401 QAGVLSGDQD TGDLVLLDVC PLTLGIETVG GVMTKLIPRN TVVPTKKSQI

451 FSTASDNQPT VTIKVYEGER PLTKDNHLLG TFDLTGIPPA PRGVPQIEVT

501 FEIDVNGILR VTAEDKGTGN KNKITITNDQ NRLTPEEIER MVNDAEKFAE

551 EDKKLKERID TRNELESYAY SLKNQIGDKE KLGGKLSSED KETMEKAVEE

601 KIEWLESHQD ADIEDFKAKK KELEEIVQPI ISKLYGSAGP PPTGEEDTAE

651 KDEL
```

SEQ ID NO:1

FIGURE 11

Protein CALR_Human..........P27797  Without signal peptide
Mw 48142Da    417 aa.  SEQ ID NO: 2    Mw 46466Da    400 aa.

Protein is without signal
Sequence of 17 aa length

```
  1  MLLSVPLLLG LLGLAVAEPA VYFKEQFLDG DGWTSRWIES KHKSDFGKFV LSSGKFYGDE
 61  EKDKGLQTSQ DARFYALSAS FEPFSNKGQT LVVQFTVKHE QNIDCGGGYV KLFPNSLDQT
121  DMHGDSEYNI MFGPDICGPG TKKVHVIFNY KGKNVLINKD IRCKDDEFTH LYTLIVRPDN
181  TYEVKIDNSQ VESGSLEDDW DFLPPKKIKD PDASKPEDWD ERAKIDDPTD SKPEDWDKPE
241  HIPDPDAKKP EDWDEEMDGE WEPPVIQNPE YKGEWKPRQI DNPDYKGTWI HPEIDNPEYS
301  PDPSIYAYDN FGVLGLDLWQ VKSGTIFDNF LITNDEAYAE EFGNETWGVT KAAEKQMKDK
361  QDEEQRLKEE EEDKKRKEEE EAEDKEDDED KDEDEEDEED KEEDEEEDVP GQAKDEL
```

| Start | End | Observed | Mr(expt) | Mr(calc) | Delta | Miss | Sequence |       |              |
|-------|-----|----------|----------|----------|-------|------|----------|-------|--------------|
| 18    | 24  | 427.2406 | 852.4664 | 852.4391 | 0.0273 | 0   | A.EPAVYFK.E |    | (Ions score: 38) |
| 18    | 24  | 427.2700 | 852.5254 | 852.4381 | 0.0873 | 0   | A.EPAVYFK.E |  | (Ions score: 20) |

The peptide begins not from lysine or arginine.
This indicates that it is N-terminal residue.

SEQUENCE LISTING

```
<160> NUMBER OF SEQ ID NOS: 6

<210> SEQ ID NO 1
<211> LENGTH: 654
<212> TYPE: PRT
<213> ORGANISM: Homo sapiens
<220> FEATURE:
<221> NAME/KEY: SIGNAL
<222> LOCATION: (1)..(18)
<220> FEATURE:
<221> NAME/KEY: mat_peptide
<222> LOCATION: (19)..(654)

<400> SEQUENCE: 1

Met Lys Leu Ser Leu Val Ala Ala Met Leu Leu Leu Leu Ser Ala Ala
        -15                 -10                  -5

Arg Ala Glu Glu Glu Asp Lys Lys Glu Asp Val Gly Thr Val Val Gly
    -1   1               5                  10

Ile Asp Leu Gly Thr Thr Tyr Ser Cys Val Gly Val Phe Lys Asn Gly
 15                  20                  25                  30

Arg Val Glu Ile Ile Ala Asn Asp Gln Gly Asn Arg Ile Thr Pro Ser
                 35                  40                  45

Tyr Val Ala Phe Thr Pro Glu Gly Glu Arg Leu Ile Gly Asp Ala Ala
                 50                  55                  60

Lys Asn Gln Leu Thr Ser Asn Pro Glu Asn Thr Val Phe Asp Ala Lys
 65                  70                  75
```

```
Arg Leu Ile Gly Arg Thr Trp Asn Asp Pro Ser Val Gln Gln Asp Ile
    80                  85                  90

Lys Phe Leu Pro Phe Lys Val Glu Lys Lys Thr Lys Pro Tyr Ile
95                  100                 105                 110

Gln Val Asp Ile Gly Gly Gln Thr Lys Thr Phe Ala Pro Glu Glu
                115                 120                 125

Ile Ser Ala Met Val Leu Thr Lys Met Lys Glu Thr Ala Glu Ala Tyr
            130                 135                 140

Leu Gly Lys Lys Val Thr His Ala Val Thr Val Pro Ala Tyr Phe
            145                 150                 155

Asn Asp Ala Gln Arg Gln Ala Thr Lys Asp Ala Gly Thr Ile Ala Gly
160                 165                 170

Leu Asn Val Met Arg Ile Ile Asn Glu Pro Thr Ala Ala Ala Ile Ala
175                 180                 185                 190

Tyr Gly Leu Asp Lys Arg Glu Gly Glu Lys Asn Ile Leu Val Phe Asp
                195                 200                 205

Leu Gly Gly Gly Thr Phe Asp Val Ser Leu Leu Thr Ile Asp Asn Gly
            210                 215                 220

Val Phe Glu Val Val Ala Thr Asn Gly Asp Thr His Leu Gly Gly Glu
        225                 230                 235

Asp Phe Asp Gln Arg Val Met Glu His Phe Ile Lys Leu Tyr Lys Lys
240                 245                 250

Lys Thr Gly Lys Asp Val Arg Lys Asp Asn Arg Ala Val Gln Lys Leu
255                 260                 265                 270

Arg Arg Glu Val Glu Lys Ala Lys Arg Ala Leu Ser Ser Gln His Gln
                275                 280                 285

Ala Arg Ile Glu Ile Glu Ser Phe Tyr Glu Gly Glu Asp Phe Ser Glu
            290                 295                 300

Thr Leu Thr Arg Ala Lys Phe Glu Glu Leu Asn Met Asp Leu Phe Arg
            305                 310                 315

Ser Thr Met Lys Pro Val Gln Lys Val Leu Glu Asp Ser Asp Leu Lys
    320                 325                 330

Lys Ser Asp Ile Asp Glu Ile Val Leu Val Gly Gly Ser Thr Arg Ile
335                 340                 345                 350

Pro Lys Ile Gln Gln Leu Val Lys Glu Phe Phe Asn Gly Lys Glu Pro
                355                 360                 365

Ser Arg Gly Ile Asn Pro Asp Glu Ala Val Ala Tyr Gly Ala Ala Val
            370                 375                 380

Gln Ala Gly Val Leu Ser Gly Asp Gln Asp Thr Gly Asp Leu Val Leu
        385                 390                 395

Leu Asp Val Cys Pro Leu Thr Leu Gly Ile Glu Thr Val Gly Gly Val
400                 405                 410

Met Thr Lys Leu Ile Pro Arg Asn Thr Val Val Pro Thr Lys Lys Ser
415                 420                 425                 430

Gln Ile Phe Ser Thr Ala Ser Asp Asn Gln Pro Thr Val Thr Ile Lys
                435                 440                 445

Val Tyr Glu Gly Glu Arg Pro Leu Thr Lys Asp Asn His Leu Leu Gly
            450                 455                 460

Thr Phe Asp Leu Thr Gly Ile Pro Pro Ala Pro Arg Gly Val Pro Gln
            465                 470                 475

Ile Glu Val Thr Phe Glu Ile Asp Val Asn Gly Ile Leu Arg Val Thr
    480                 485                 490

Ala Glu Asp Lys Gly Thr Gly Asn Lys Asn Lys Ile Thr Ile Thr Asn
```

```
            495                 500                 505                 510
Asp Gln Asn Arg Leu Thr Pro Glu Glu Ile Glu Arg Met Val Asn Asp
                515                 520                 525

Ala Glu Lys Phe Ala Glu Glu Asp Lys Lys Leu Lys Glu Arg Ile Asp
                530                 535                 540

Thr Arg Asn Glu Leu Glu Ser Tyr Ala Tyr Ser Leu Lys Asn Gln Ile
                545                 550                 555

Gly Asp Lys Glu Lys Leu Gly Gly Lys Leu Ser Ser Glu Asp Lys Glu
                560                 565                 570

Thr Met Glu Lys Ala Val Glu Glu Lys Ile Glu Trp Leu Glu Ser His
575                 580                 585                 590

Gln Asp Ala Asp Ile Glu Asp Phe Lys Ala Lys Lys Glu Leu Glu
                    595                 600                 605

Glu Ile Val Gln Pro Ile Ile Ser Lys Leu Tyr Gly Ser Ala Gly Pro
                610                 615                 620

Pro Pro Thr Gly Glu Glu Asp Thr Ala Glu Lys Asp Glu Leu
                625                 630                 635

<210> SEQ ID NO 2
<211> LENGTH: 417
<212> TYPE: PRT
<213> ORGANISM: Homo sapiens
<220> FEATURE:
<221> NAME/KEY: SIGNAL
<222> LOCATION: (1)..(17)
<220> FEATURE:
<221> NAME/KEY: mat_peptide
<222> LOCATION: (18)..(417)

<400> SEQUENCE: 2

Met Leu Leu Ser Val Pro Leu Leu Leu Gly Leu Leu Gly Leu Ala Val
            -15                 -10                  -5

Ala Glu Pro Ala Val Tyr Phe Lys Glu Gln Phe Leu Asp Gly Asp Gly
 -1   1               5                  10                  15

Trp Thr Ser Arg Trp Ile Glu Ser Lys His Lys Ser Asp Phe Gly Lys
                 20                  25                  30

Phe Val Leu Ser Ser Gly Lys Phe Tyr Gly Asp Glu Glu Lys Asp Lys
             35                  40                  45

Gly Leu Gln Thr Ser Gln Asp Ala Arg Phe Tyr Ala Leu Ser Ala Ser
             50                  55                  60

Phe Glu Pro Phe Ser Asn Lys Gly Gln Thr Leu Val Val Gln Phe Thr
 65                  70                  75

Val Lys His Glu Gln Asn Ile Asp Cys Gly Gly Gly Tyr Val Lys Leu
 80                  85                  90                  95

Phe Pro Asn Ser Leu Asp Gln Thr Asp Met His Gly Asp Ser Glu Tyr
                100                 105                 110

Asn Ile Met Phe Gly Pro Asp Ile Cys Gly Pro Gly Thr Lys Lys Val
                115                 120                 125

His Val Ile Phe Asn Tyr Lys Gly Lys Asn Val Leu Ile Asn Lys Asp
                130                 135                 140

Ile Arg Cys Lys Asp Asp Glu Phe Thr His Leu Tyr Thr Leu Ile Val
145                 150                 155

Arg Pro Asp Asn Thr Tyr Glu Val Lys Ile Asp Asn Ser Gln Val Glu
160                 165                 170                 175

Ser Gly Ser Leu Glu Asp Asp Trp Asp Phe Leu Pro Pro Lys Lys Ile
                180                 185                 190
```

```
Lys Asp Pro Asp Ala Ser Lys Pro Glu Asp Trp Asp Glu Arg Ala Lys
            195                 200                 205

Ile Asp Asp Pro Thr Asp Ser Lys Pro Glu Asp Trp Asp Lys Pro Glu
            210                 215                 220

His Ile Pro Asp Pro Asp Ala Lys Lys Pro Glu Asp Trp Asp Glu Glu
            225                 230                 235

Met Asp Gly Glu Trp Glu Pro Pro Val Ile Gln Asn Pro Glu Tyr Lys
240                 245                 250                 255

Gly Glu Trp Lys Pro Arg Gln Ile Asp Asn Pro Asp Tyr Lys Gly Thr
                260                 265                 270

Trp Ile His Pro Glu Ile Asp Asn Pro Glu Tyr Ser Pro Asp Pro Ser
            275                 280                 285

Ile Tyr Ala Tyr Asp Asn Phe Gly Val Leu Gly Leu Asp Leu Trp Gln
            290                 295                 300

Val Lys Ser Gly Thr Ile Phe Asp Asn Phe Leu Ile Thr Asn Asp Glu
            305                 310                 315

Ala Tyr Ala Glu Glu Phe Gly Asn Glu Thr Trp Gly Val Thr Lys Ala
320                 325                 330                 335

Ala Glu Lys Gln Met Lys Asp Lys Gln Asp Glu Glu Gln Arg Leu Lys
                340                 345                 350

Glu Glu Glu Glu Asp Lys Lys Arg Lys Glu Glu Glu Glu Ala Glu Asp
            355                 360                 365

Lys Glu Asp Asp Glu Asp Lys Asp Glu Asp Glu Glu Asp Glu Glu Asp
            370                 375                 380

Lys Glu Glu Asp Glu Glu Glu Asp Val Pro Gly Gln Ala Lys Asp Glu
385                 390                 395

Leu
400

<210> SEQ ID NO 3
<211> LENGTH: 505
<212> TYPE: PRT
<213> ORGANISM: Homo sapiens
<220> FEATURE:
<221> NAME/KEY: SIGNAL
<222> LOCATION: (1)..(24)
<220> FEATURE:
<221> NAME/KEY: mat_peptide
<222> LOCATION: (25)..(505)

<400> SEQUENCE: 3

Met Arg Leu Arg Arg Leu Ala Leu Phe Pro Gly Val Ala Leu Leu Leu
                -20                 -15                 -10

Ala Ala Ala Arg Leu Ala Ala Ala Ser Asp Val Leu Glu Leu Thr Asp
            -5                  -1  1                   5

Asp Asn Phe Glu Ser Arg Ile Ser Asp Thr Gly Ser Ala Gly Leu Met
            10                  15                  20

Leu Val Glu Phe Phe Ala Pro Trp Cys Gly His Cys Lys Arg Leu Ala
25                  30                  35                  40

Pro Glu Tyr Glu Ala Ala Ala Thr Arg Leu Lys Gly Ile Val Pro Leu
                45                  50                  55

Ala Lys Val Asp Cys Thr Ala Asn Thr Asn Thr Cys Asn Lys Tyr Gly
            60                  65                  70

Val Ser Gly Tyr Pro Thr Leu Lys Ile Phe Arg Asp Gly Glu Glu Ala
            75                  80                  85

Gly Ala Tyr Asp Gly Pro Arg Thr Ala Asp Gly Ile Val Ser His Leu
            90                  95                  100
```

Lys Lys Gln Ala Gly Pro Ala Ser Val Pro Leu Arg Thr Glu Glu
105                 110                 115                 120

Phe Lys Lys Phe Ile Ser Asp Lys Asp Ala Ser Ile Val Gly Phe Phe
                125                 130                 135

Asp Asp Ser Phe Ser Glu Ala His Ser Glu Phe Leu Lys Ala Ala Ser
            140                 145                 150

Asn Leu Arg Asp Asn Tyr Arg Phe Ala His Thr Asn Val Glu Ser Leu
        155                 160                 165

Val Asn Glu Tyr Asp Asp Asn Gly Glu Gly Ile Ile Leu Phe Arg Pro
170                 175                 180

Ser His Leu Thr Asn Lys Phe Glu Asp Lys Thr Val Ala Tyr Thr Glu
185                 190                 195                 200

Gln Lys Met Thr Ser Gly Lys Ile Lys Lys Phe Ile Gln Glu Asn Ile
                205                 210                 215

Phe Gly Ile Cys Pro His Met Thr Glu Asp Asn Lys Asp Leu Ile Gln
                220                 225                 230

Gly Lys Asp Leu Leu Ile Ala Tyr Tyr Asp Val Asp Tyr Glu Lys Asn
            235                 240                 245

Ala Lys Gly Ser Asn Tyr Trp Arg Asn Arg Val Met Met Val Ala Lys
250                 255                 260

Lys Phe Leu Asp Ala Gly His Lys Leu Asn Phe Ala Val Ala Ser Arg
265                 270                 275                 280

Lys Thr Phe Ser His Glu Leu Ser Asp Phe Gly Leu Glu Ser Thr Ala
                285                 290                 295

Gly Glu Ile Pro Val Val Ala Ile Arg Thr Ala Lys Gly Glu Lys Phe
                300                 305                 310

Val Met Gln Glu Glu Phe Ser Arg Asp Gly Lys Ala Leu Glu Arg Phe
            315                 320                 325

Leu Gln Asp Tyr Phe Asp Gly Asn Leu Lys Arg Tyr Leu Lys Ser Glu
330                 335                 340

Pro Ile Pro Glu Ser Asn Asp Gly Pro Val Lys Val Val Ala Glu
345                 350                 355                 360

Asn Phe Asp Glu Ile Val Asn Asn Glu Asn Lys Asp Val Leu Ile Glu
                365                 370                 375

Phe Tyr Ala Pro Trp Cys Gly His Cys Lys Asn Leu Glu Pro Lys Tyr
            380                 385                 390

Lys Glu Leu Gly Glu Lys Leu Ser Lys Asp Pro Asn Ile Val Ile Ala
        395                 400                 405

Lys Met Asp Ala Thr Ala Asn Asp Val Pro Ser Pro Tyr Glu Val Arg
        410                 415                 420

Gly Phe Pro Thr Ile Tyr Phe Ser Pro Ala Asn Lys Lys Leu Asn Pro
425                 430                 435                 440

Lys Lys Tyr Glu Gly Gly Arg Glu Leu Ser Asp Phe Ile Ser Tyr Leu
                445                 450                 455

Gln Arg Glu Ala Thr Asn Pro Pro Val Ile Gln Glu Glu Lys Pro Lys
            460                 465                 470

Lys Lys Lys Lys Ala Gln Glu Asp Leu
        475                 480

<210> SEQ ID NO 4
<211> LENGTH: 1965
<212> TYPE: DNA
<213> ORGANISM: Homo sapiens

<400> SEQUENCE: 4

```
atgaagctct ccctggtggc cgcgatgctg ctgctgctca gcgcggcgcg ggccgaggag      60
gaggacaaga aggaggacgt gggcacggtg gtcggcatcg acctggggac cacctactcc     120
tgcgtcggcg tgttcaagaa cggccgcgtg gagatcatcg ccaacgatca gggcaaccgc     180
atcacgccgt cctatgtcgc cttcactcct gaaggggaac gtctgattgg cgatgccgcc     240
aagaaccagc tcacctccaa ccccgagaac acggtctttg acgccaagcg gctcatcggc     300
cgcacgtgga atgacccgtc tgtgcagcag gacatcaagt tcttgccgtt caaggtggtt     360
gaaaagaaaa ctaaaccata cattcaagtt gatattggag gtgggcaaac aaagacattt     420
gctcctgaag aaatttctgc catggttctc actaaaatga agaaaccgc tgaggcttat      480
ttgggaaaga aggttaccca tgcagttgtt actgtaccag cctattttaa tgatgcccaa     540
cgccaagcaa ccaaagacgc tggaactatt gctggcctaa atgttatgag gatcatcaac     600
gagcctacgg cagctgctat tgcttatggc ctgataaga gggaggggga aagaacatc       660
ctggtgtttg acctgggtgg cggaaccttc gatgtgtctc ttctcaccat tgacaatggt     720
gtcttcgaag ttgtggccac taatggagat actcatctgg gtggagaaga ctttgaccag     780
cgtgtcatgg aacacttcat caaactgtac aaaaagaaga cgggcaaaga tgtcaggaaa     840
gacaatagag ctgtgcagaa actccggcgc gaggtagaaa aggccaaacg ggccctgtct     900
tctcagcatc aagcaagaat tgaaattgag tccttctatg aaggagaaga cttttctgag     960
accctgactc gggccaaatt tgaagagctc aacatggatc tgttccggtc tactatgaag    1020
cccgtccaga agtgttggaa gagattctgat ttgaagaagt ctgatattga tgaaattgtt    1080
cttgttggtg gctcgactcg aattccaaag attcagcaac tggttaaaga gttcttcaat    1140
ggcaaggaac catcccgtgg cataaaccca gatgaagctg tagcgtatgg tgctgctgtc    1200
caggctggtg tgctctctgg tgatcaagat acaggtgacc tggtactgct tgatgtatgt    1260
cccttacac ttggtattga aactgtggga ggtgtcatga ccaaactgat tccaaggaac    1320
acagtggtgc ctaccaagaa gtctcagatc ttttctacag cttctgataa tcaaccaact    1380
gttacaatca aggtctatga aggtgaaaga cccctgacaa aagacaatca tcttctgggt    1440
acatttgatc tgactggaat tcctcctgct cctcgtgggg tcccacagat tgaagtcacc    1500
tttgagatag atgtgaatgg tattcttcga gtgacagctg aagacaaggg tacagggaac    1560
aaaaataaga tcacaatcac caatgaccag aatcgcctga cacctgaaga aatcgaaagg    1620
atggttaatg atgctgagaa gtttgctgag gaagacaaaa agctcaagga gcgcattgat    1680
actagaaatg agttggaaag ctatgcctat tctctaaaga atcagattgg agataaagaa    1740
aagctgggag gtaaactttc ctctgaagat aaggagacca tggaaaaagc tgtagaagaa    1800
aagattgaat ggctggaaag ccaccaagat gctgacattg aagactcaa agctaagaag    1860
aaggaactgg aagaaattgt tcaaccaatt atcagcaaac tctatggaag tgcaggcccct    1920
cccccaactg gtgaagagga tacagcagaa aaagatgagt tgtag                    1965
```

<210> SEQ ID NO 5
<211> LENGTH: 1254
<212> TYPE: DNA
<213> ORGANISM: Homo sapiens

<400> SEQUENCE: 5

```
atgctgctat ccgtgccgtt gctgctcggc ctcctcggcc tggccgtcgc cgagcctgcc      60
gtctacttca aggagcagtt tctggacgga gacgggtgga cttcccgctg gatcgaatcc     120
```

```
aaacacaagt cagattttgg caaattcgtt ctcagttccg gcaagttcta cggtgacgag      180
gagaaagata aaggtttgca gacaagccag gatgcacgct tttatgctct gtcggccagt      240
ttcgagcctt tcagcaacaa aggccagacg ctggtggtgc agttcacggt gaaacatgag      300
cagaacatcg actgtggggg cggctatgtg aagctgtttc ctaatagttt ggaccagaca      360
gacatgcacg gagactcaga atacaacatc atgtttggtc ccgacatctg tggccctggc      420
accaagaagg ttcatgtcat cttcaactac aagggcaaga acgtgctgat caacaaggac      480
atccgttgca aggatgatga gtttacacac ctgtacacac tgattgtgcg gccagacaac      540
acctatgagg tgaagattga caacagccag gtggagtccg gctccttgga agacgattgg      600
gacttcctgc cacccaagaa gataaaggat cctgatgctt caaaaccgga agactgggat      660
gagcgggcca agatcgatga tcccacagac tccaagcctg aggactggga caagcccgag      720
catatccctg accctgatgc taagaagccc gaggactggg atgaagagat ggacggagag      780
tgggaacccc cagtgattca gaaccctgag tacaagggtg agtggaagcc ccggcagatc      840
gacaacccag attacaaggg cacttggatc cacccagaaa ttgacaaccc cgagtattct      900
cccgatccca gtatctatgc ctatgataac tttggcgtgc tgggcctgga cctctggcag      960
gtcaagtctg gcaccatctt tgacaacttc ctcatcacca acgatgaggc atacgctgag     1020
gagtttggca cgagacgtg gggcgtaaca aaggcagcag agaaacaaat gaaggacaaa     1080
caggacgagg agcagaggct taaggaggag gaagaagaca gaaacgcaa agaggaggag     1140 gaggcagagg acaaggagga tgatgaggac aaagatgagg atgaggagga tgaggaggac     1200
aaggaggaag atgaggagga agatgtcccc ggccaggcca aggacgagct gtag           1254

<210> SEQ ID NO 6
<211> LENGTH: 1518
<212> TYPE: DNA
<213> ORGANISM: Homo sapiens

<400> SEQUENCE: 6
atgcgcctcc gccgcctagc gctgttcccg ggtgtggcgc tgcttcttgc cgcggcccgc       60
ctcgccgctg cctccgacgt gctagaactc acggacgaca acttcgagag tcgcatctcc      120
gacacgggct ctgcgggcct catgctcgtc gagttcttcg ctccctggtg tggacactgc      180
aagagacttg cacctgagta tgaagctgca gctaccagat aaaaggaat agtcccatta      240 gcaaaggttg attgcactgc caacactaac acctgtaata aatatggagt cagtggatat      300
ccaaccctga agatatttag agatggtgaa gaagcaggtg cttatgatgg acctaggact      360
gctgatggaa ttgtcagcca cttgaagaag caggcaggac cagcttcagt gcctctcagg      420
actgaggaag aatttaagaa attcattagt gataaagatg cctctatagt aggtttttc      480 gatgattcat tcagtgaggc tcactccgag ttcctaaaag cagccagcaa cttgagggat      540
aactaccgat ttgcacatac gaatgttgag tctctggtga acgagtatga tgataatgga      600
gagggtatca tcttatttcg tccttcacat ctcactaaca agtttgagga caagactgtg      660
gcatatacag agcaaaaaat gaccagtggc aaaattaaaa agtttatcca ggaaaacatt      720
tttggtatct gccctcacat gacagaagac aataaagatt tgataccaggg caaggactta      780 cttattgctt actatgatgt ggactatgaa agaacgctaa aggttccaa ctactggaga      840 aacagggtaa tgatggtggc aaagaaattc ctggatgctg gcacaaaact caactttgct      900
gtagctagcc gcaaaacctt tagccatgaa ctttctgatt ttggcttgga gagcactgct      960
```

-continued

```
ggagagattc ctgttgttgc tatcagaact gctaaaggag agaagtttgt catgcaggag    1020
gagttctcgc gtgatgggaa ggctctggag aggttcctgc aggattactt tgatggcaat    1080
ctgaagagat acctgaagtc tgaacctatc ccagagagca atgatgggcc tgtgaaggta    1140
gtggtagcag agaattttga tgaaatagtg aataatgaaa ataaagatgt gctgattgaa    1200
ttttatgccc cttggtgtgg tcattgtaag aacctggagc ccaagtataa agaacttggc    1260
gagaagctca gcaaagaccc aaatatcgtc atagccaaga tggatgccac agccaatgat    1320
gtgccttctc catatgaagt cagaggtttt cctaccatat acttctctcc agccaacaag    1380
aagctaaatc caaagaaata tgaaggtggc cgtgaattaa gtgattttat tagctatcta    1440
caaagagaag ctacaaaccc ccctgtaatt caagaagaaa aacccaagaa gaagaagaag    1500
gcacaggagg atctctaa                                                  1518
```

GENERATION OF NATIVE RECOMBINANT SECRETED HUMAN ENDOPLASMIC RETICULUM CHAPERONES BY USING THEIR NATIVE SIGNAL SEQUENCES IN YEAST EXPRESSION SYSTEMS

RELATED APPLICATIONS

This application is a Continuation of, and claims, priority under 35 U.S.C. §120 to, International Application No. PCT/US2013/049843, filed Jul. 10, 2013, and claims priority therethrough under 35 U.S.C. §119 to U.S. Provisional Application No. 61/670,768 filed Jul. 12, 2012, the entireties of which are incorporated by reference herein.

BACKGROUND

Endoplasmic reticulum (ER) chaperones are multifunctional proteins involved in a variety of biological processes such as protein folding and quality control in the ER (Hebert et al., 1995; Zhang et al., 1997; Braakman & van Anken, 2000; High et al., 2000; Bedard et al., 2005; Benyair et al., 2011; Braakman & Bulleid, 2011), unfolded protein response (Spear & Ng, 2001; Ma & Hendershot, 2004; Malhotra & Kaufman, 2007; Groenendyk et al., 2010; Chakrabarti et al., 2011), MHC class I antigen processing (Maffei et al., 1997; Nicchitta & Reed, 2000; Zhang & Williams, 2006; Wearsch & Cresswell, 2009), as well as other important functions these proteins play outside of the ER (Panayi & Corrigall, 2006; Gonzalez-Gronow et al. 2009; Gold et al., 2010; Ni et al., 2011; Peters & Raghavan, 2011; Turano et al., 2011). The role of ER chaperones in various human diseases seems especially important. There are growing amounts of data demonstrating involvement of particular ER chaperones in many pathological processes. For example, ER chaperone GRP78/BiP appears to be involved in cancer progression (Li & Lee, 2006; Lee, 2007; Luo & Lee, 2012), autoimmune inflammation and tissue damage (Panayi & Corrigall, 2006; Morito & Nagata, 2012) and rheumatoid arthritis (Corrigall et al., 2001; Yoo et al., 2012). Another ER chaperone calreticulin plays an important role in activating the anti-tumor response needed in chemotherapy or various other cancer treatment strategies (Chaput et al., 2007; Obeid et al., 2007; Wemeau et al., 2010) and is also associated with the healing processes of cutaneous wounds (Nanney et al., 2008). Other ER chaperones have also been implicated in disease related processes, such as prion diseases in the case of chaperone GRP58/ERp57 (Hetz et al., 2005). These recent findings suggest possible application of ER chaperones in therapeutic trials and development of new pharmaceuticals. Therefore, the growing demand of human ER chaperone protein products could be expected in the near future.

Native human ER chaperone proteins can be purified from various tissues, e.g. calreticulin has been purified from human placenta (Houen & Koch, 1994), however human tissues are not a sufficient source of these proteins for large scale clinical trials. The recombinant protein expression technologies should be considered for efficient and safe production of these proteins. Furthermore, it is desirable that the recombinant proteins for clinical trials should correspond to native analogs insofar as possible.

Currently most recombinant human ER chaperones are produced in bacterial host *Escherichia coli* (Rokeach et al., 1991; Baksh et al., 1992; Antoniou et al., 2002) and such products are commercially available (Abcam products ab78432, ab91577 and ab92937, 2012; StressMarq product SPR-119B, 2012; USBiological products B1770-01, C1036-02L1 and E2291-75E, 2012). However, *E. coli* and other prokaryotes do not possess the ER, Golgi apparatus and other organelles of the eukaryotic secretion pathway, therefore it is uncertain that human ER proteins produced in bacteria will be correctly folded and possess all the same functions as the native protein analogues. Yeast is an attractive host for the production of the ER chaperones and other complex secreted human proteins, because this unicellular eukaryotic microorganism has eukaryotic features including a secretory pathway leading to correct protein processing and post-translational modifications (Mattanovich et al., 2012). Many attempts have being made to generate recombinant secreted human proteins in yeast (Damasceno et al., 2012; Hou et al., 2012) as such expression system facilitates purification and downstream processing of the protein product and the secreted proteins often are biologically active. Regarding generation of the secreted human ER chaperone proteins in yeast, several techniques may be used. All these approaches include use of the conventional yeast protein secretion signal fused to the sequence of processed mature human ER protein. The protein product generated in this way has several non-native amino acids on the N-terminus and the effect of this manipulation to biological activity of the prepared proteins is unclear. The only known example of yeast-expressed secreted full-length recombinant mammalian ER chaperone described in the literature so far is generation of recombinant rabbit calreticulin in yeast *Pichia pastoris* (Andrin et al., 2000).

SUMMARY OF THE INVENTION

No attempts to use native signal sequences of human ER chaperones in microbial hosts to produce correctly processed final native recombinant ER chaperone products in the same way as in the native analogs in human cells are known. Use of the native signal sequences of several intracellular human ER chaperones for the secretion of correctly processed final products to the culture media in yeast *S. cerevisiae* and *P. pastoris* expression systems is described herein. Surprisingly, this approach enabled generation of large amounts of native recombinant human chaperones processed in the same way as in human cells, except that mature protein products were secreted into yeast culture medium. The invention also shows experimental data that confirm correct processing of the signal sequences of human ER chaperones in yeast cells and provides how to efficiently produce these proteins in secreted form.

The present invention provides methods for producing native recombinant human ER chaperones in yeast with a simple downstream purification procedure. These proteins do not have any added artificial amino acid sequences and are processed into the final products, which exactly correspond to analogue human proteins according to their predicted molecular weight. This is achieved by integrating several key factors, as described below, and is only true for human endoplasmic reticulum (ER) luminal proteins. The results show how the method functions by describing the procedure with three human ER proteins as examples.

The present invention encompasses methods for producing recombinant proteins. These methods including the steps of
  (a) transforming a yeast cell with a nucleotide sequence comprising the coding sequence for a native human ER chaperone protein signal sequence and a human ER chaperone protein;

(b) culturing the yeast cell under conditions such that the human ER recombinant chaperone protein is expressed in secreted form; and (c) extracting the human ER recombinant chaperone protein from the culture medium.

One embodiment of the method in accord with the present invention produces a human ER recombinant chaperone protein, where the human ER chaperone protein is a human ER luminal protein. The method includes the steps of culturing a yeast cell, the yeast cell having been transformed with a nucleotide sequence comprising the coding sequence for both a native human ER chaperone protein signal sequence and a human ER chaperone protein, under conditions to express the human ER recombinant chaperone protein in secreted form; and extracting the human ER recombinant chaperone protein from the culture medium.

Another embodiment of the method in accord with the present invention produces a human ER recombinant chaperone protein selected from the group consisting of BiP/GRP78, calreticulin, and ERp57. The method includes the steps of (a) providing a yeast cell transformed with a nucleotide sequence comprising the coding sequence for both a native human ER chaperone protein signal sequence and a human ER chaperone protein;

(b) culturing the yeast cell under conditions such that the human ER recombinant chaperone protein is expressed in secreted form; and (c) extracting at least one of BiP/GRP78, calreticulin, or ERp57 from the culture medium.

Methods accord with the present invention may yield up to about 100 mg/L of the desired protein and the yield may be further increased by optimization of yeast culturing conditions by conventional methods well known in the art.

Another embodiment of the method in accord with the present invention produces human ER recombinant chaperone proteins by (a) providing a yeast cell transformed with a nucleotide sequence comprising the coding sequence for both a native human ER chaperone protein signal sequence and a human ER chaperone protein;

(b) culturing the yeast cell under conditions such that the human ER recombinant chaperone protein is expressed in secreted form; and (c) extracting the human ER recombinant chaperone protein from the culture medium.

BRIEF DESCRIPTION OF THE DRAWINGS

FIG. 5 shows location of the tryptic peptide mass fingerprinting of *S. cerevisiae*-secreted GRP78/BiP protein band by using MALDI-TOF/TOF tandemic MS/MS (mass spectrometry) together with UPLC/MS$^E$ method.

DETAILED DESCRIPTION

The invention encompasses yeast expression systems for the synthesis of native recombinant secreted human ER chaperone proteins in yeast cells. Yeasts are unicellular eukaryotic microorganisms capable of performing eukaryotic processing on the expressed polypeptides. Since yeast represent eukaryotes, their intracellular environment is more suitable for a correct folding of eukaryotic proteins including human cell proteins. Yeast-derived heterologous proteins are free of toxic contaminations and are excellent tools for developing vaccines, diagnostics or biopharmaceuticals. The yeast Saccharomyces cerevisiae is acknowledged as GRAS (generally regarded as safe) organism. The mostly native recombinant human or virus proteins generated in yeast possess similar properties as native proteins from human cells and are superior over their analogues expressed in bacteria. The growing demand for various recombinant proteins of high quality necessitates better and more efficient expression systems, even for the proteins with well-established production protocols. Native human proteins for various purposes are often purified from various human cells, as recombinant protein is synthesized and purified from Escherichia coli using various tags. The present invention demonstrated that yeast was by far a superior host for expression and purification of native recombinant human proteins.

ER chaperones are multifunctional proteins involved in a variety of biological processes such as protein folding and quality control in the ER, unfolded protein response, MHC class I antigen processing, and other important functions these proteins play outside of the ER. The role of ER chaperones in various human diseases appears especially important, with data demonstrating involvement of particular ER chaperones in many pathological processes. These recent findings suggest possible application of ER chaperones in therapeutic trials and development of new pharmaceuticals, along with fundamental and applied studies. Recombinant protein expression technologies provide efficient and safe production of these proteins. Examples provided here include, but are not limited to, GRP78/BiP, calreticulin and GRP58/ERp57 that are produced in yeast cells. The resultant proteins produced by the inventive method are tag-free. No tags were used for purification of these recombinant proteins; however, proteins could be His-tagged as well. The resultant proteins produced by the inventive method were correctly processed in yeast cell and the final protein product was composed from exactly the same amino acid sequence as in human cells. Non-native modifications were not present in the resultant recombinant products. The oligomeric state of the resultant recombinant proteins corresponded to that of native human chaperone proteins isolated from human tissues. The resultant recombinant proteins produced by the inventive method were fully active and were stable.

Figure 1:
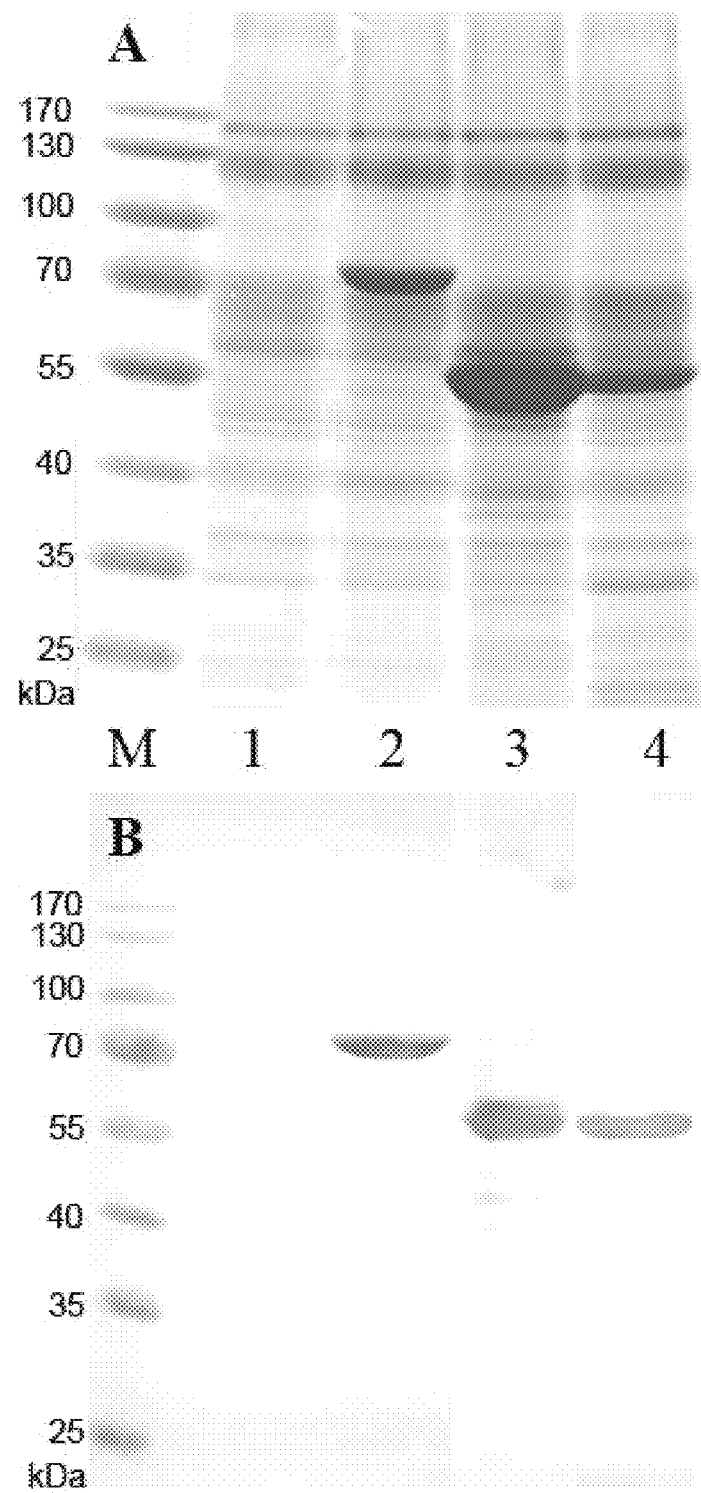
FIG. 1 shows SDS-PAGE (panel A) and Western blot (panel B) analysis of 40× concentrated culture media of yeast *S. cerevisiae* AH22 cells transformed with empty plasmid (lane 1) or producing human chaperones BiP, calreticulin and ERp57 (lanes 2, 3 and 4, respectively).

Three human ER proteins were used as examples in the disclosed procedure. Human genes HSPA5 (SEQ ID NO:4), CALR (SEQ ID NO:5), and PDIA3 (SEQ ID NO:6) (GeneBank id. no. respectively AF216292, M84739 and U42068), coding human ER chaperones, BiP/GRP78 (SEQ ID NO:1), calreticulin (SEQ ID NO:2), and ERp57 (SEQ ID NO:3), were cloned from commercial human liver cDNA library (Clonetech, USA). The cDNA of the human genes was cloned intact, without any changes to the sequences coding signal sequences, ER retention signals. The functional parts of the proteins were not removed, modified, or replaced with any homologous sequences from genes of the yeast or any other species. After nucleotide sequence analysis, human genes HSPA5, CALR, and PDIA3 were cloned into the yeast expression vector pFDC under control of yeast PGK1 gene promoter as described (Ciplys et al., 2011), resulting in three recombinant plasmids pFDC-BiP, pFDC-CALR, and pFDC-ERp57. pFDC-BiP, pFDC-CALR and pFDC-ERp57 yeast expression vectors, carrying human genes, were used for transformation of S. cerevisiae strain AH22 MATa (leu2 his4). Yeast transformation and subsequent selection of transformants were carried out exactly as described (Ciplys et al, 2011). After cultivation of yeast cells carrying recombinant plasmids in YEPD medium (yeast extract 1%, peptone 2%, dextrose 2%), proteins of yeast cells and growth medium were analyzed. Surprisingly, recombinant human chaperones were not only found in membrane protein fractions of the yeast cells, as previously described (Ciplys et al, 2011), but were also found in fairly large amounts in the growth medium, where they constituted up to about 50-60% of all proteins, as shown in FIG. 1.

About 1 L of culture medium contained 40 mg-50 mg secreted human calreticulin protein and 10 mg-15 mg of BiP/GRP78 and ERp57 proteins. The identity of the proteins was confirmed by Western blot analysis using specific antibodies against each human chaperone (FIG. 1 (panel A): lane 2—rabbit polyclonal antibodies against human BiP/GRP78 (Ab21685, Abcam, UK); lane 3—mouse monoclonal antibodies against human calreticulin (Ab22683, Abcam, UK); and lane 4—mouse monoclonal antibodies against human ERp57 (Ab13506, Abcam, UK). This observed phenomenon of high-level secretion of human ER chaperones using their whole cDNA nucleotide sequences without any changes in yeast was never described previously.

To further analyze the process, human HSPA5, CALR, and PDIA3 genes were cloned into the yeast expression vectors, similar to pFDC, but under different promoters of other yeast genes, ADH2, TDH2, TPI1, TEF, and ENO2. For expression of human BiP, calreticulin, and ERp57 proteins, different yeast S. cerevisiae strains were used (8188c, AH-214u, AH-214uΔpep4). The results obtained using different promoters and strains were very similar to those shown in FIG. 1. This demonstrated that secretion of native amino acid sequence human chaperones into the yeast growth media was not associated with use of certain promoters or strains for their synthesis, but rather was a conjunction of different properties of the yeast cell: (i) ability to recognize signal sequence of human proteins and translocate them into the ER, but (ii) inability to retain human chaperones in their destined cell compartment. These properties were not discovered and/or utilized for production of native recombinant human proteins in yeast.

It should be noted that signal peptides of human chaperones actually are not secretion signal amino acid sequences, because they are used only for direction of native human proteins to the ER. When signal sequences are cleaved, chaperones in human cells are retained in the ER. Even though in some cases native human chaperones were shown to be directed to the cell surface, they were not secreted outside the cell. In fact, human ER chaperones are known as intracellular proteins. Therefore, here we for the first time show capabilities of yeast cells to secrete intracellular human proteins using their native signal sequences for intracellular processing and transfer of mature proteins inside the cell. It is known that some secreted human proteins may be secreted in yeast cells using their native secretion signal sequences (Hitzeman et al, 1983; Barr et al, 1992). This process was patented in 1988 using human interferons as examples (Hitzeman and Leung, 1988) and also used in 1994 for patenting expression of human serum albumin using its native secretion signal sequence in *P. pastoris* (Prevatt and Sreekrishna, 1994). However, in the most cases *S. cerevisiae* α-MF prepro signal sequence was used for the secretion of other heterologous proteins in yeast, because native secretion signal sequences were less efficient (Cereghino and Cregg, 2000). Our findings are different from previous observations that native signal sequences may drive secretion of secreted human proteins in yeast. It may be expected that secreted human proteins will also be secreted in yeast cells using the same signal sequence. In contrast, the secretion of intracellular human proteins, such as ER-resident chaperones, is not expected for recombinantly expressed analogues in yeast. Moreover, the secretion level of human ER chaperones in yeast is unexpectedly high and allows efficient production of correctly processed recombinant products. Taken together, we present in principle new protocols for secretion of heterologous human proteins in the yeast cells.

All three secreted human chaperones were then purified and analyzed. Purification of secreted recombinant human chaperones from culture media was performed using standard procedures such as microfiltration, ultrafiltration, and one-step chromatography, and standard protocols. This simple purification procedure was sufficient to achieve over 90% purity of native recombinant human chaperones. Such simple and effective downstream purification procedure was another advantage of the disclosed expression system. N-terminal sequencing by Edman degradation was performed for identification and characterization of purified secreted proteins. Edman sequencing (performed using a service of AltaBioscience) of the chaperone products from *S. cerevisiae* in all three cases identified the five N-terminal amino acids and showed that they corresponded to mature native chaperone products from human cells (see Table 1: $NH_2$-EEEDK for GRP78/BiP; $NH_2$-EPAVY for calreticulin, and $NH_2$-SDVLE for ERp57). These results indicate that native ER signal sequences of human chaperone proteins are recognized and correctly processed in yeast cells, and this allows translocation of recombinant proteins into the ER following unexpected secretion outside the yeast cell. To check for possible modifications of secreted protein products we performed electrospray mass spectrometry (ESI-MS) analysis of a whole protein molecule to determine the exact molecular masses of yeast-secreted human ER chaperones. Results of mass spectrometry are given in Table 1 and FIG. 2A-2C; Table 1 indicates the exact determined molecular masses of the products and predicted molecular weights.

TABLE 1

N-terminal sequence, predicted and determined molecular weight of secreted recombinant human chaperones purified from *S. cerevisiae*.

| Protein | N-terminal sequence of the protein with indicated signal peptide[1] | Predicted[2] molecular weight of whole protein | Predicted[2] molecular weight of protein without signal sequence | Results of mass spectrometery of recombinant secreted human chaperones | N-terminal Edman sequencing of recombinant secreted human chaperones |
|---|---|---|---|---|---|
| BiP | MKLSLVAAML LLLSAARAEE EDKKEDVGTV... | 72332.96 | 70478.57 | 70478.39 | $NH_2$-EEEDK |
| Calreticulin | MLLSVPLLLG LLGLAVAEPA VYFKEQFLDG... | 48141.56 | 46466.37 | 46466.09 | $NH_2$-EPAVY |
| ERp57 | MRLRRLALPP GVALLLAAAR LAAASDVLEL... | 56782.39 | 54265.22 | 54265.55 | $NH_2$-SDVLE |

[1]N-terminal sequences with indicated signal peptides were taken from UniProtKB database, reviewed entries P11021 (GRP78_HUMAN), P27797 (CALR_HUMAN) and P30101 (PDIA3_HUMAN) for BiP, calreticulin and ERp57, respectively. Sequences of cleaved signal peptides are highlighted, whereas mature protein sequences are indicated in bold.
[2]Predicted molecular weights for BiP, calreticulin and ERp57 were calculated using free software tools in the same UniProtKB database sources.

Figure 2A:
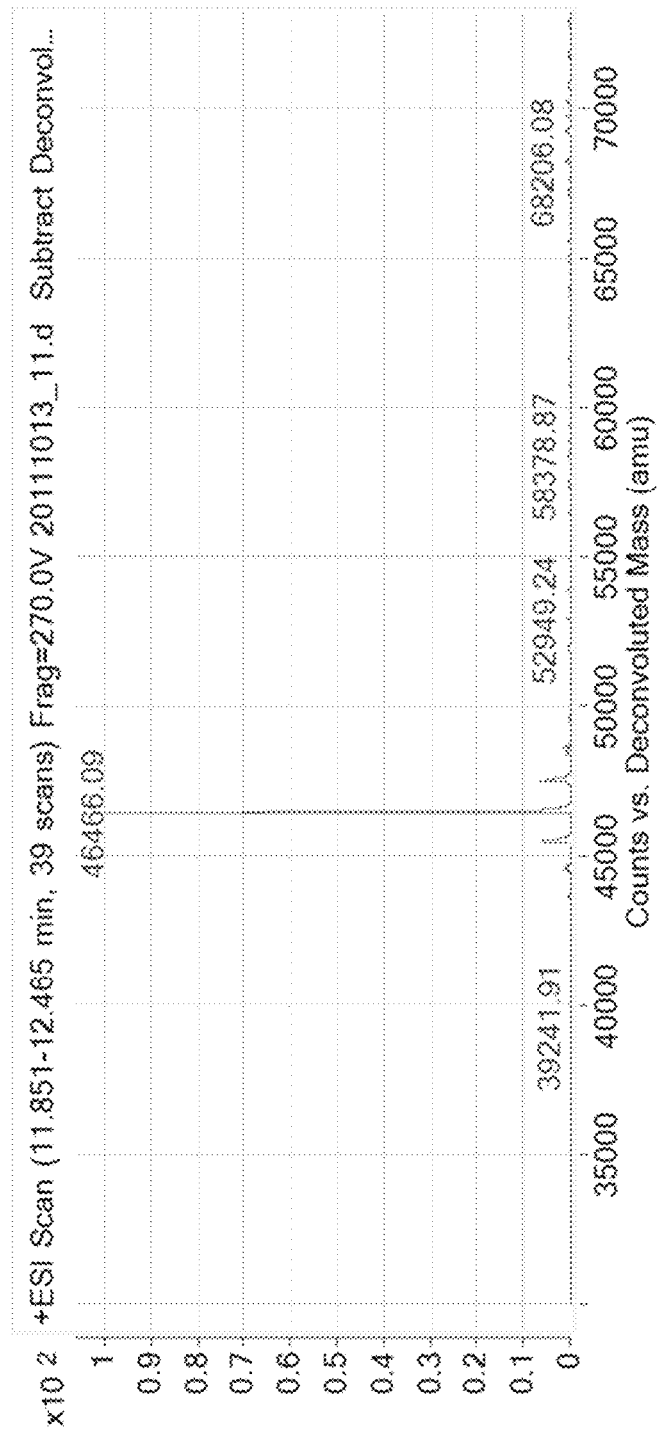
FIG. 2A shows ESI-MS of secreted recombinant human chaperones calreticulin.
Figure 2B:
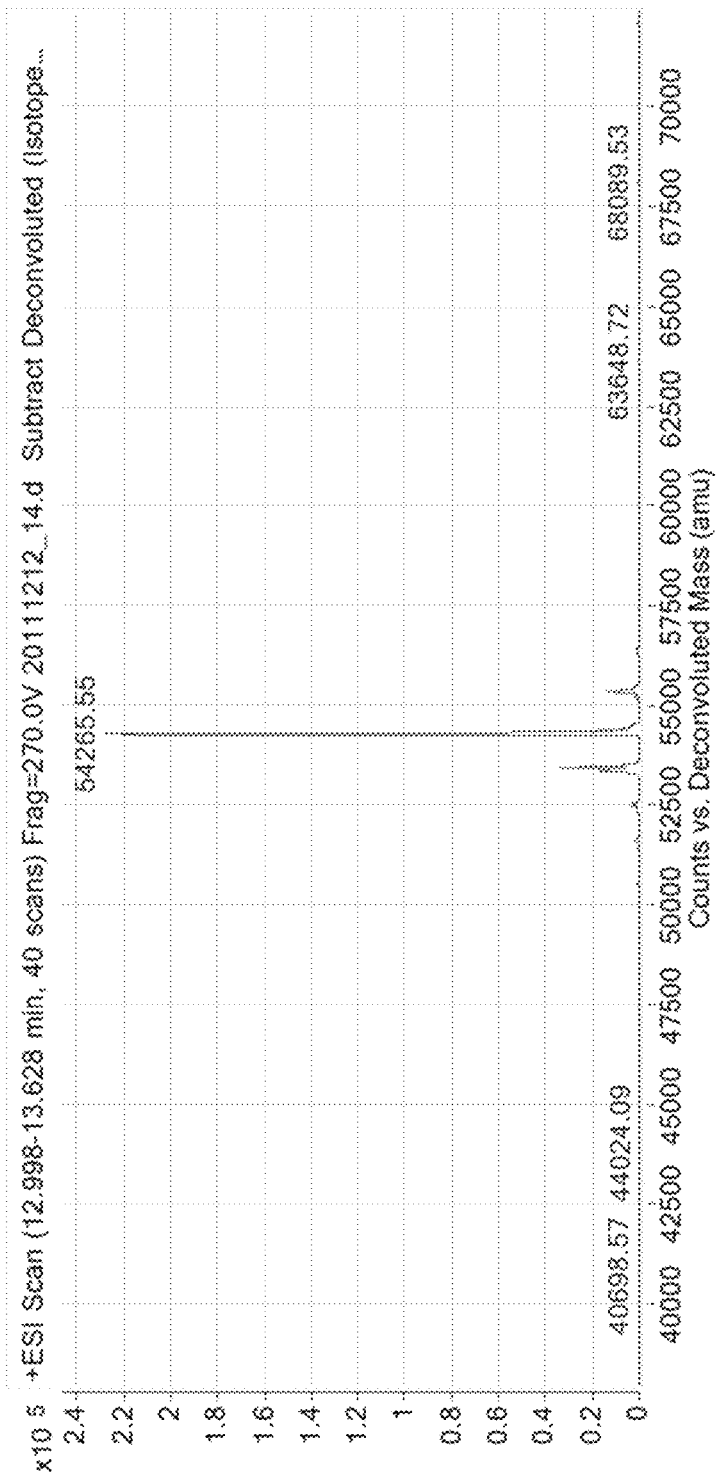
FIG. 2B shows ESI-MS of ERp57.
Figure 2C:
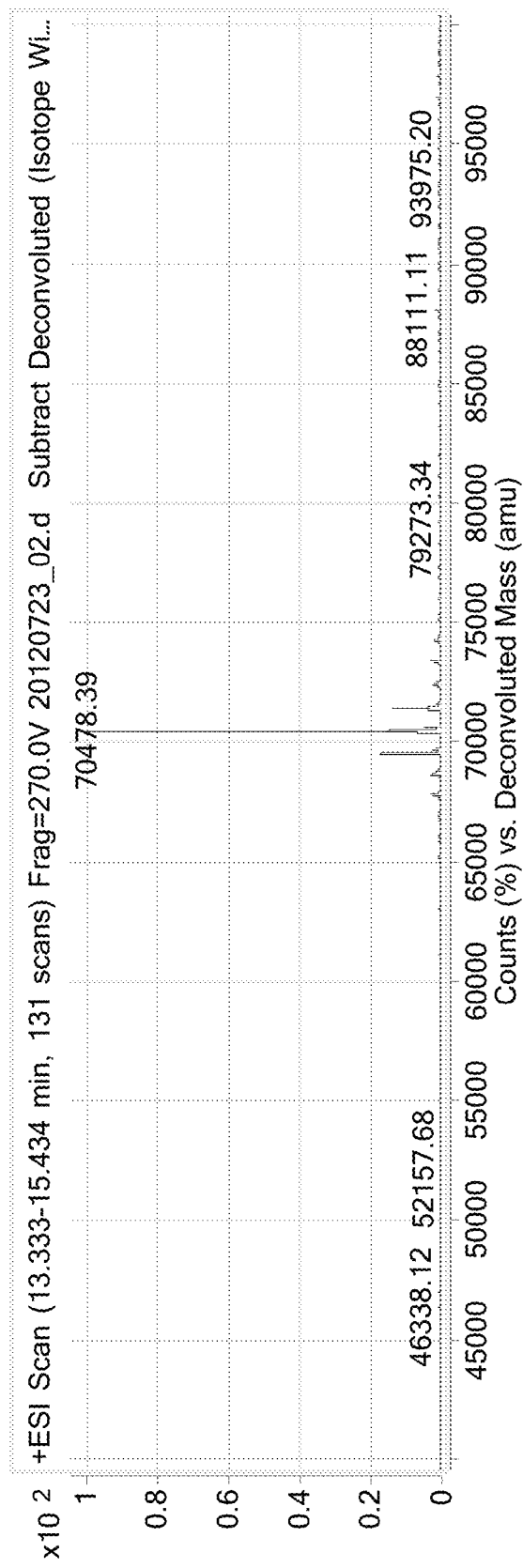
FIG. 2C shows ESI-MS of GRP78/BiP purified from *S. cerevisiae*.

Mass spectrometry results of yeast *S. cerevisiae*-derived purified human BiP, calreticulin and ERp57 proteins showed the masses of 70478.39, 46466.09 and 54265.55, respectively, which exactly correspond to theoretically predicted masses of mature human proteins (FIG. 2A-2C and Table 1). It indicates two things: (i) recombinant secreted human BiP, calreticulin and ERp57 proteins are exactly the same polypeptides as mature human ER proteins (including predicted ER retention signals KDEL or QEDL on the C-termini of the proteins) and (ii) they have no yeast-derived modifications—a very important characteristic for recombinant proteins. Moreover, mass spectrometry analysis revealed that the proteins were highly pure (FIG. 2A-2C).

Mass spectrometry results together with N-terminal sequencing of the secreted recombinant human BiP, calreticulin, and ERp57 proteins clearly showed that all three human chaperones were correctly processed in yeast cells. In the eukaryotic cells signal peptides of maturating proteins are recognized by translocon machinery that ensures proper translocation of protein into the ER. After the polypeptides are translocated in the ER lumen signal peptides are cleaved by a signal peptide peptidase complex that is located inside the ER (Zimmermann et al, 2011). No data exists about compatibility of human and yeast translocon machinery or signal peptide peptidase complex. The data disclosed herein show that specificity of these complexes from both species was generally the same, thus the signal sequence of maturating human chaperone in yeast cells was correctly recognized by yeast proteins, resulting in proper cleavage of signal peptide following successful translocation of human protein into the ER. This phenomenon was never employed for the secreted production of intracellular recombinant human proteins in yeast cells. As mentioned, for secretion of recombinant proteins in various yeast species, the yeast secretion signal sequences are fused to target proteins resulting in several additional non-native amino acids adhered to the protein after secretion. The disclosed method not only simplified cloning of human genes for expression in yeast cells, but also ensured that recombinant human protein has exactly the same composition of amino acids as in human cells.

Thus, the identification of the N-termini of recombinant human BiP, calreticulin and ERp57 confirmed the results of mass spectrometry, namely, that secreted human chaperones purified from yeast S. cerevisiae had intact native amino acid sequences. ER retrieval sequences of all three proteins were also intact (KDEL amino acids in BiP and calreticulin, and QEDL in ERp57). Retrieval machinery of eukaryotic cells recognizes proteins that possess retrieval signals and retains them in the ER lumen (Capitani & Sallese, 2009). This indicated that the recombinant human chaperones were secreted from S. cerevisiae despite the presence of the ER retrieval signal. It raises question about reasons of secretion of human proteins by yeast cells and about retention of proteins in the ER in general. A leaky retention signal was described previously (Andrin et al., 2000; Hamilton & Gerngross, 2007) but was never utilized for production of secreted native recombinant proteins. Secretion of human ER proteins by S. cerevisiae cells could be explained by yeast preference for the HDEL rather than KDEL or QEDL signal for efficient retrieval of the ER-resident proteins (Dean and Pelham, 1990), but it was not the reason in this case, because replacement of KDEL or QEDL with the HDEL sequence did not suppress the secretion of BiP, calreticulin and ERp57 (our unpublished data). Also, overload of the yeast ER retrieval machinery can be omitted as the reason for secretion of human ER proteins, because overexpression of yeast Kar2 protein with native HDEL ER retrieval sequence using the same pFDC vector did not lead to the secretion of this protein (our unpublished data). Moreover, human PDI, which is homologue of human ERp57 and yeast PDI proteins and contains KDEL ER retrieval sequence, was also expressed using the same pFDC vector, and in this case secretion of recombinant protein was not observed (our unpublished data). These experiments indicate that retention of ER luminal proteins is complicated and still unsolved mechanism, which does not strictly depend on HDEL/KDEL retrieval mechanism. Our finding, secretion of human ER chaperones by yeast cells, could serve as a convenient model for studying this phenomenon. On the other hand, this process may be exploited for efficient production of native recombinant human ER proteins in yeasts.

Taking together, these results clearly demonstrated that a newly discovered phenomenon of the ability of yeast cells to recognize and correctly process signal sequence of human ER proteins, with subsequent secretion of mature products to the culture media, provides new opportunities for synthesis of recombinant ER chaperones in yeast. The inventive findings allow synthesis of secreted native recombinant human chaperones with a simple downstream purification procedure. Moreover, recombinant human proteins passed the protein secretion pathway of yeast cells, which might ensure their proper maturation.

The present invention also encompasses other yeast expression systems including, but not limited to, P. pastoris. The same cDNA constructs encoding full sequences of human chaperones with native signal sequences for the secretion of protein products were used. Secretion of all three protein products was shown (see the Examples). The expression of GRP78/BiP and calreticulin (Examples 1 and 2) was more efficient in the P. pastoris system, which can be used to considerably enhance the product yields. SDS-PAGE images of P. pastoris culture media samples for both BiP and CRT proteins illustrate efficiency of secretion in this host (FIG. 3 (panels A and B). Initially, the amount of secreted ERp57 in P. pastoris was lower than in S. cerevisiae. However, after optimization of cultivation conditions of P. pastoris culture, the amount of secreted human ERp57 exceeded that of S. cerevisiae cells (FIG. 3 (panel C). Optimized protocol for the expression of ERp57 in P. pastoris is provided in the Example 3. After secretion to the culture media, human BiP, calreticulin and ERp57 proteins were purified from P. pastoris by using the same methods as in the case of expression in S. cerevisiae. The properties of purified products were similar to those of analogous proteins derived from S. cerevisiae cells (more detailed description of the experiments is given in the Examples). Therefore, our invention refers to generation of human ER chaperones in yeasts in general, rather to the expression in one yeast species.

Figure 7:
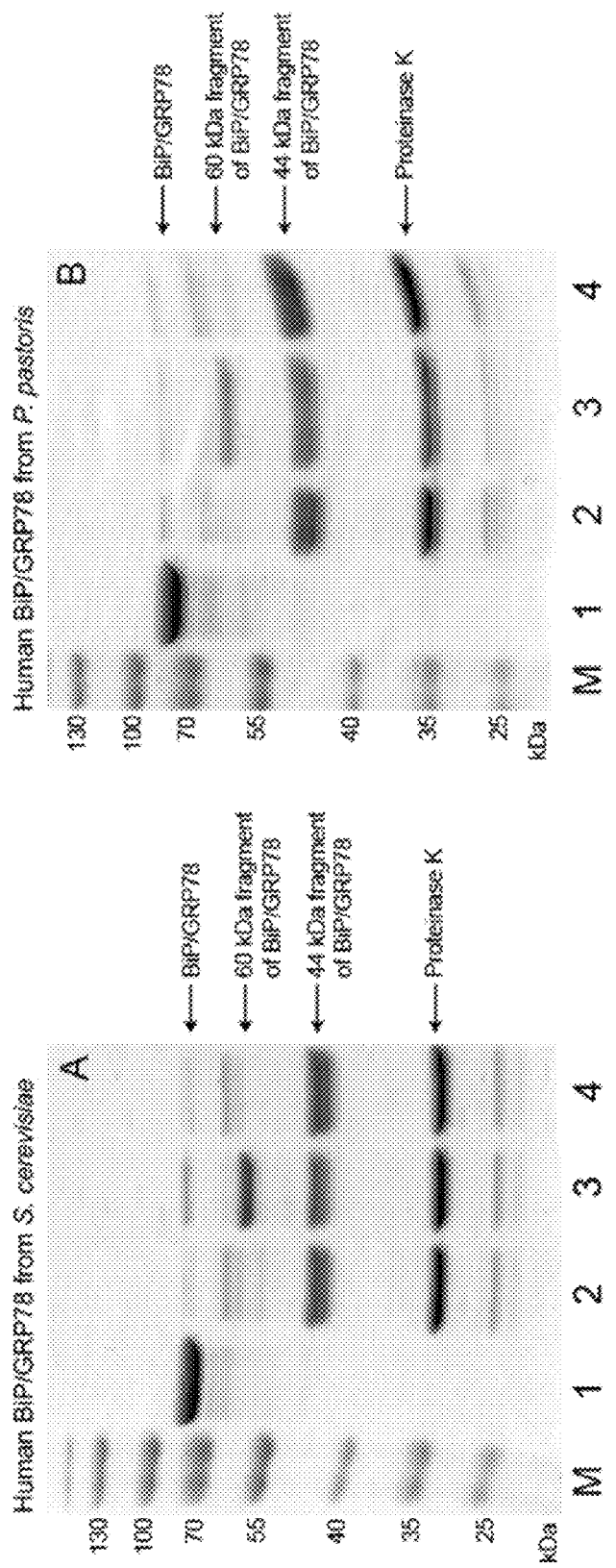
FIG. 7 shows partial proteolysis of recombinant BiP protein purified from *S. cerevisiae* (panel A) and *P. pastoris* (panel B).
Figure 8:
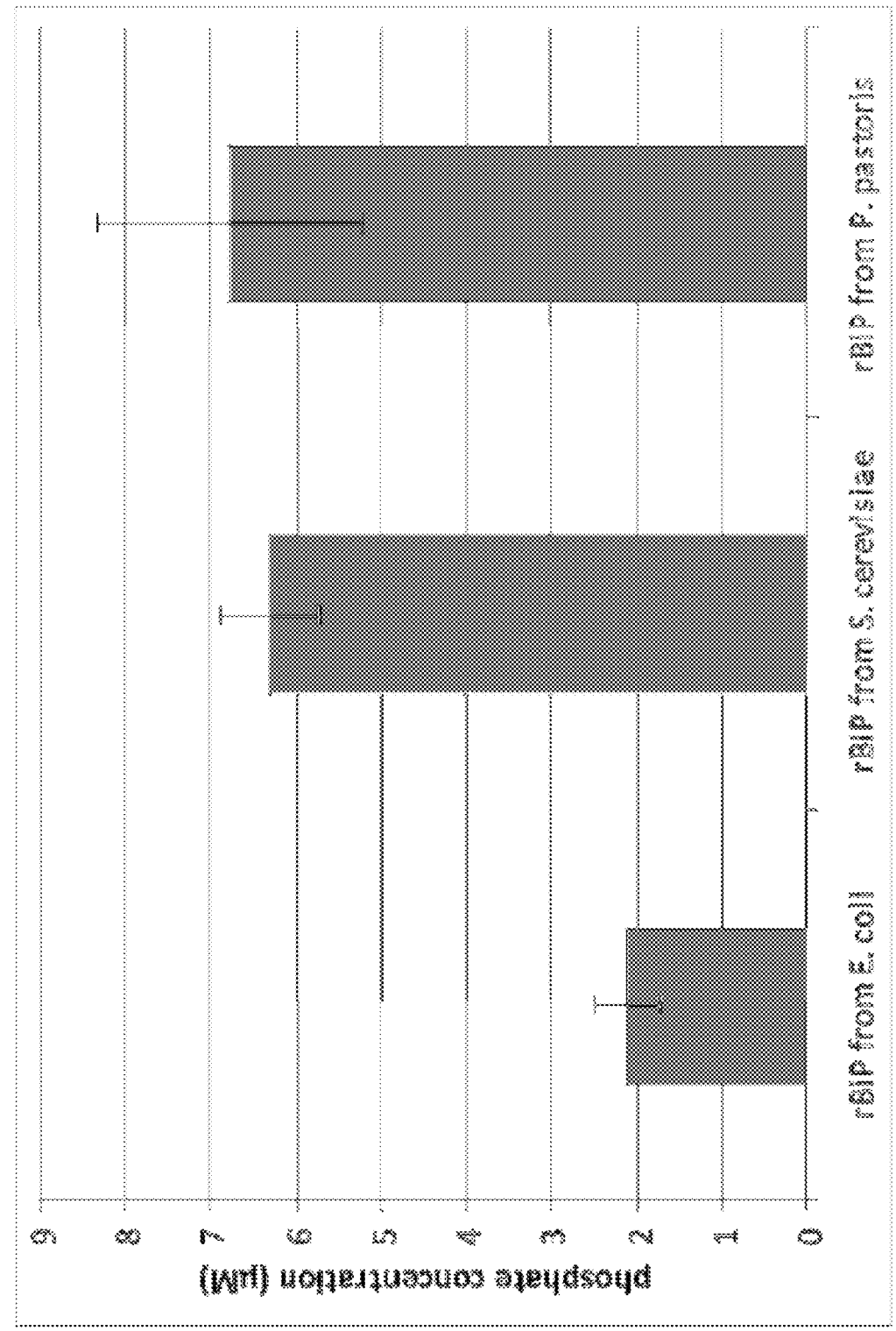
FIG. 8 shows ATPase activity test using recombinant BiP proteins expressed in bacteria and yeasts.
Figure 19:
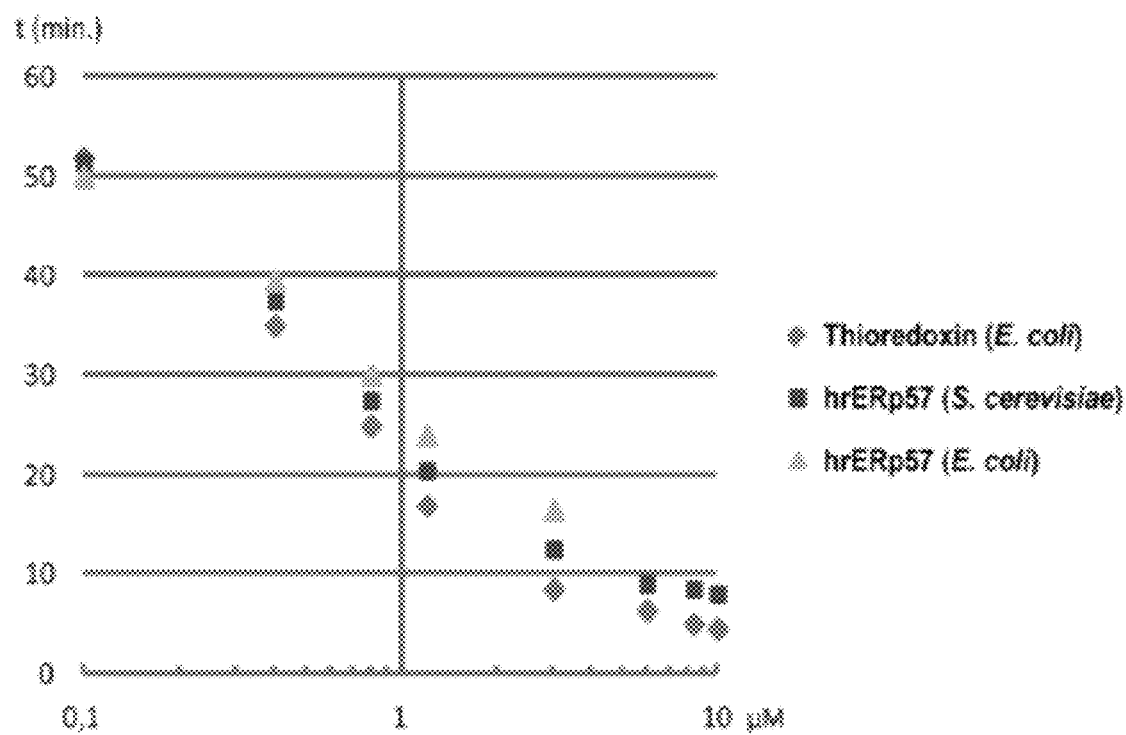
FIG. 19 shows thiol-dependent catalytic activity of yeast-derived recombinant human ERp57 protein assayed with the insulin precipitation method.

Finally, we claim for the generation of biologically active human ER chaperones in yeast. Here we show that all three yeast-derived human proteins BiP, calreticulin and ERp57 are correctly folded and possess biological activity. GRP78/BiP protein produced in accord with the disclosed invention showed correct folding and activity of the product. Yeast-expressed BiP protein bound ATP, and this protected a ~60 kDa fragment from proteolysis by proteinase K (FIG. 7). Similar data was previously used to demonstrate correct folding of E. coli expressed analogous protein. For activity of yeast-expressed protein, an ATP-ase activity test of GRP78/BiP was used, also using an E. coli expressed analog as parallel control. As shown in FIG. 8, there was three-fold higher yeast-expressed secreted BiP chaperone activity than that of commercial E. coli product (~6.3 µM versus ~2.1 µM of hydrolysed ATP by the same amount of protein in the same time). ATP binding and protection of ~60 kDa domain of P. pastoris-derived BiP was similar to that from S. cerevisiae (FIG. 7 (panel B). The ATP-ase activity of P. pastoris-expressed BiP was also measured and showed similar results as for S. cerevisiae-expressed analog (FIG. 8, the average for P. pastoris-expressed BiP was slightly higher than for S. cerevisiae analog, but within the range of error) with about three fold increase compared to E. coli-expressed product. This considerable difference demonstrated an advantage of yeast-expressed products. Partial digestion of calreticulin with trypsin (Corbett et al., 2000; Højrup et al., 2001) suggested correct folding and $Ca^{2+}$ binding of yeast-expressed hCRT, as it is shown in Example 2. Furthermore, in vitro assay for cellular proliferation (Nanney et al., 2008; Greives et al., 2012) showed slightly but significantly higher induction of human fibroblast proliferation by both S. cerevisiae- and P. pastoris-derived human calreticulin compared to the same protein purified from bacteria E. coli (Table 2 and FIG. 14). Moreover, wound healing scratch plate assay showed that both E. coli- and yeast-expressed recombinant calreticulin induce migration of human fibroblasts at the similar extent within the range of error (Table 3 and FIG. 15). Taken together, the data of yeast-expressed human calreticulin demonstrated that recombinant product possesses at least the same biological activity as recombinant calreticulin derived from bacteria. It should be noted that the same *E. coli*-expressed calreticulin protein, used as a control in these assays, previously has shown profound effects on the process of wound healing in vivo by causing a dose-dependent increase in epithelial migration and granulation tissue formation in both murine and porcine normal and impaired animal models of skin injury (Gold et al., 2006; Greives et al., 2012). Therefore, it could be expected that the yeast-derived secreted human calreticulin may also be successfully used for wound healing in vivo. Regarding ERp57, the data showed thiol-dependent reductase activity of ERp57 chaperone. Comparing *S. cerevisiae*-expressed ERp57 chaperone product with the same commercially available recombinant chaperone expressed in bacteria *E. coli*, the data demonstrated that yeast-expressed protein was slightly but considerably more active than the same amount of ERp57 analog expressed in *E. coli* (FIG. 19). Therefore, the disclosed system could generate more active product than in *E. coli* and provides an efficient platform for the production of recombinant ER chaperones.

The invention will be further appreciated with reference to the following non-limiting examples.

Example 1

Figure 3:
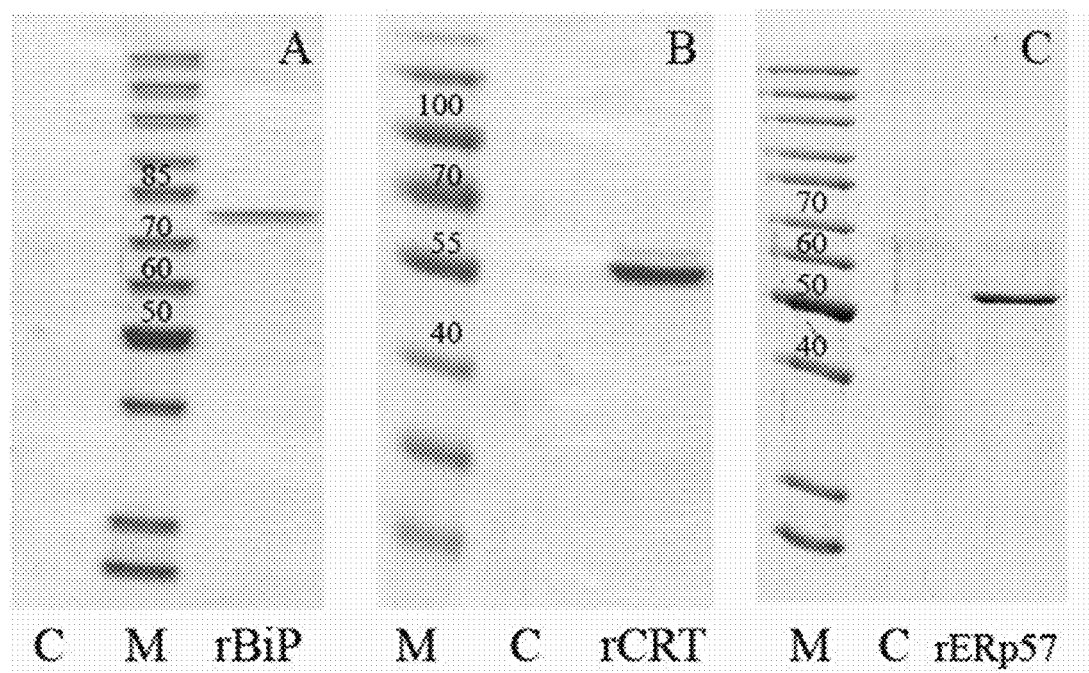
FIG. 3 shows SDS-PAGE of unconcentrated culture media (8 μl each) from selected *P. pastoris* GS115 strain multicopy transformants overexpressing secreted recombinant human BiP (panel A), calreticulin (panel B) and ERp57 (panel C). C indicates control (8 μl of unconcentrated culture media from *P. pastoris* GS115 strain transformed with empty vector pPIC3.5K without human gene and cultured in parallel to strains overexpressing human chaperones), whereas M—protein markers with known molecular weights indicated over the bands.

Generation of Native Recombinant Human GRP78/BiP Protein in Yeast Expression Systems Human BiP/GRP78 is a major endoplasmic reticulum chaperone which plays a dual role in the ER by controlling protein folding, in order to prevent aggregation, and by regulating the signaling of the unfolded protein response (UPR). It also participates in many other important cellular processes, such as calcium homeostasis, apoptosis regulation and signal transduction. Recently, it has been shown that this protein is of importance in cancerous cells and it could potentially be used for therapeutic purposes. Also, growing body of evidence indicates GRP78 as a new therapeutic target for treatments of forebrain ischemia, Parkinson disease and retinal degeneration (Gorbatyuk and Gorbatyuk, 2013). In this study we present evidences, that yeasts *Saccharomyces cerevisiae* and *Pichia pastoris* are perfect hosts for expression and purification of native recombinant human BiP/GRP78 protein. The newly discovered ability of the yeast cells to recognize and correctly process native signal sequence of human BiP/GRP78 protein consequently secreting it into the growth media, allows simple one-step purification of highly pure recombinant BiP/GRP78 protein with yields reaching 10 mg/L and 20 mg/L from *S. cerevisiae* and *P. pastoris* respectively. The data showed that it was fully intact and active protein without yeast derived modifications. Yeast-derived human BiP/GRP78 protein possesses ATPase activity, which 3-fold exceeds activity of *E. coli*-derived recombinant human BiP/GRP78.

cDNA encoding full-length human GRP78/BiP (gene HSPA5 Acc. no. AF216292) was amplified from commercial human adult liver cDNA library (Clontech) by PCR using specific oligonucleotide primers BiPF (gta tct aga aca atg aag ctc tcc ctg gtg g) and BiPR (cag tct aga cta caa ctc atc ttt ttc tgc tgt), digested with restriction endonuclease (RE) XbaI and cloned into yeast expression vectors pFDC (Čiplys et al., 2011) and pPIC3.5K (Intvitrogen) into RE sites XbaI and AvrII under control of *S. cerevisiae* PGK1 or *P. pastoris* AOX1 promoters, respectively. Cloned HSPA5 gene sequence (beginning from start codon ATG and ending with STOP codon TAG) was verified by DNA sequencing and generated plasmids pFDC-BiP and pPIC3.5K-BiP were used for transformation of yeast *S. cerevisiae* and *P. pastoris*, respectively. *S. cerevisiae* transformants were selected by resistance to formaldehyde and harboured multicopy autonomously replicating plasmid pFDC-BiP, whereas multicopy *P. pastoris* transformants were selected by resistance to G418 according to standard procedure well known in the art and strains with the most efficient secretion of BiP protein were chosen for further experiments. Both yeasts were used for expression of the full length GRP78/BiP protein including native N-terminal signal peptide. Both *S. cerevisiae* and *P. pastoris* secreted GRP78/BiP protein product into the culture media. The secretion was more efficient in the selected *P. pastoris* clone. 40 times concentrated culture medium of yeast *S. cerevisiae* AH22 strain transformed with plasmid pFDC-BiP is shown in FIG. 1 (lanes 2), whereas 8 microliters of unconcentrated culture medium from the most efficient selected *P. pastoris* clone is shown in FIG. 3, panel A (lane rBiP; lane C represents control medium from *P. pastoris* transformed with empty vector pPIC3.5K without a human gene, whereas lane M—protein markers with indicated molecular weights).

After expression of recombinant human BiP, cells were separated from the medium by centrifugation and yeast growth medium was further prefiltered with subsequent microfiltration of secreted protein through 0.2 μM filter. After microfiltration, proteins were concentrated and transferred into the binding buffer (20 mM HEPES, 50 mM NaCl, 10 mM $MgCl_2$, pH 7.5) through tangential ultrafiltration using cassettes with 50 kDa cut-off membranes. Further, proteins were mixed with 8AH-ATP-agarose (Jena Bioscience) equilibrated in the same buffer and incubated for 2-3 hours at 4° C. in batch format. Unbound proteins were removed by washing with 20 column volumes of binding buffer while bound proteins were eluted with equal column volume of elution buffer (20 mM HEPES, 50 mM NaCl, 10 mM $MgCl_2$, 5 mM ATP, pH 7.5). Elution fractions were analyzed by SDS-PAGE. Three subsequent elution fractions showed ~95% pure human GRP78/BiP protein. These fractions were pooled and dialysed against ATPase buffer (50 mM HEPES, 50 mM NaCl, 2 mM $MgCl_2$, 5 mM ATP, pH 6.8) or BiP storage buffer (20 mM Tris-HCl, 350 mM NaCl, 0.5 mM DTT, 10% glycerol, pH 8.0). Such purification procedure was enough to reach ~95% purity of secreted recombinant human BiP. Yields obtained were approx. 10 mg and 20 mg from 1 L culture medium in *S. cerevisiae* and *P. pastoris* expression systems, respectively.

Figure 4:
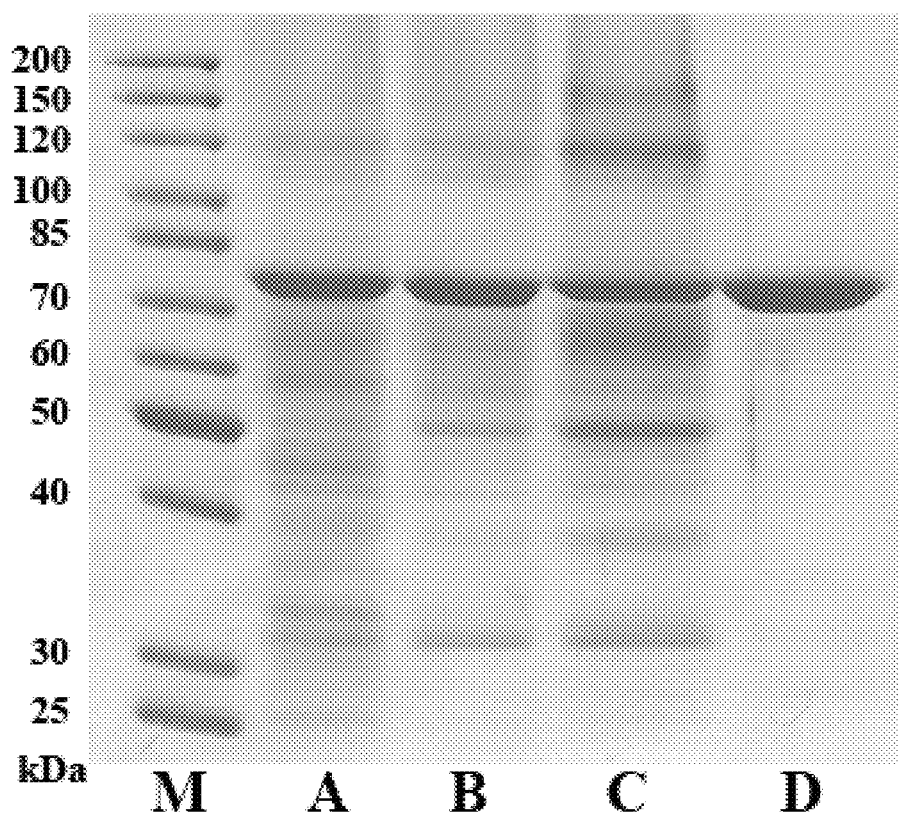
FIG. 4 shows purification of secreted recombinant human GRP78/BiP protein from yeast *S. cerevisiae* culture medium. Lanes represent protein molecular weight markers (M), yeast culture medium after human BiP expression in *S. cerevisiae* (A), the same yeast growth medium after microfiltration (B), the same medium after tangential ultrafiltration (C) and secreted recombinant human BiP protein purified by ATP-affinity chromatography from the same medium (D).

FIG. 4 shows SDS-PAGE analysis of yeast culture media and purified recombinant human BiP sample from *S. cerevisiae*. A—yeast culture medium after human BiP expression in *S. cerevisiae* (20× concentrated medium supernatant); B—yeast growth medium after microfiltration; C—20× concentrated proteins from yeast growth medium after tangential ultrafiltration; D—3 μg of secreted recombinant human BiP protein purified by ATP-affinity chromatography from *S. cerevisiae*. M—protein markers with molecular weights indicated at the left. SDS-PAGE analysis of human BiP purification from *P. pastoris* is not shown, but it is similar to that of *S. cerevisiae*.

Figure 6:
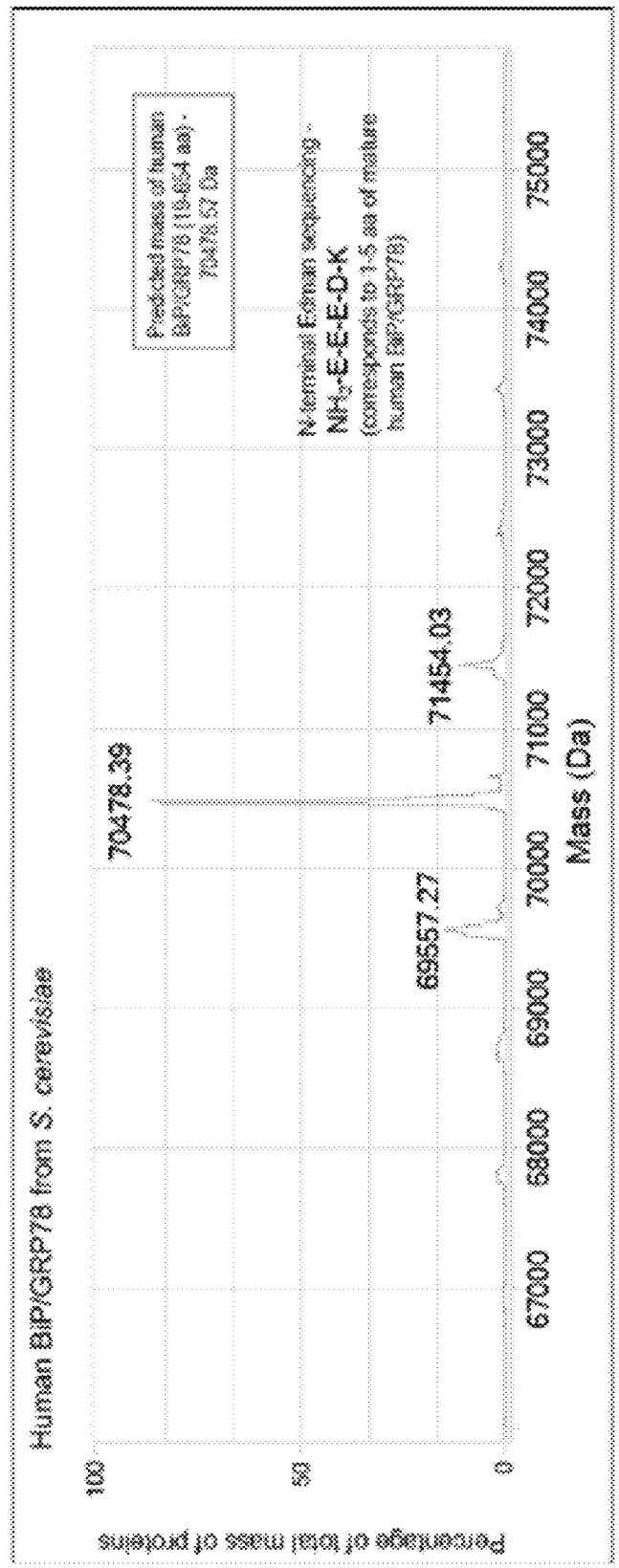
FIG. 6 shows the results of N-terminal sequencing by Edman degradation and ESI-MS of a whole molecule of recombinant human GRP78/BiP secreted from *S. cerevisiae* and *P. pastoris*, respectively.
Figure 6:
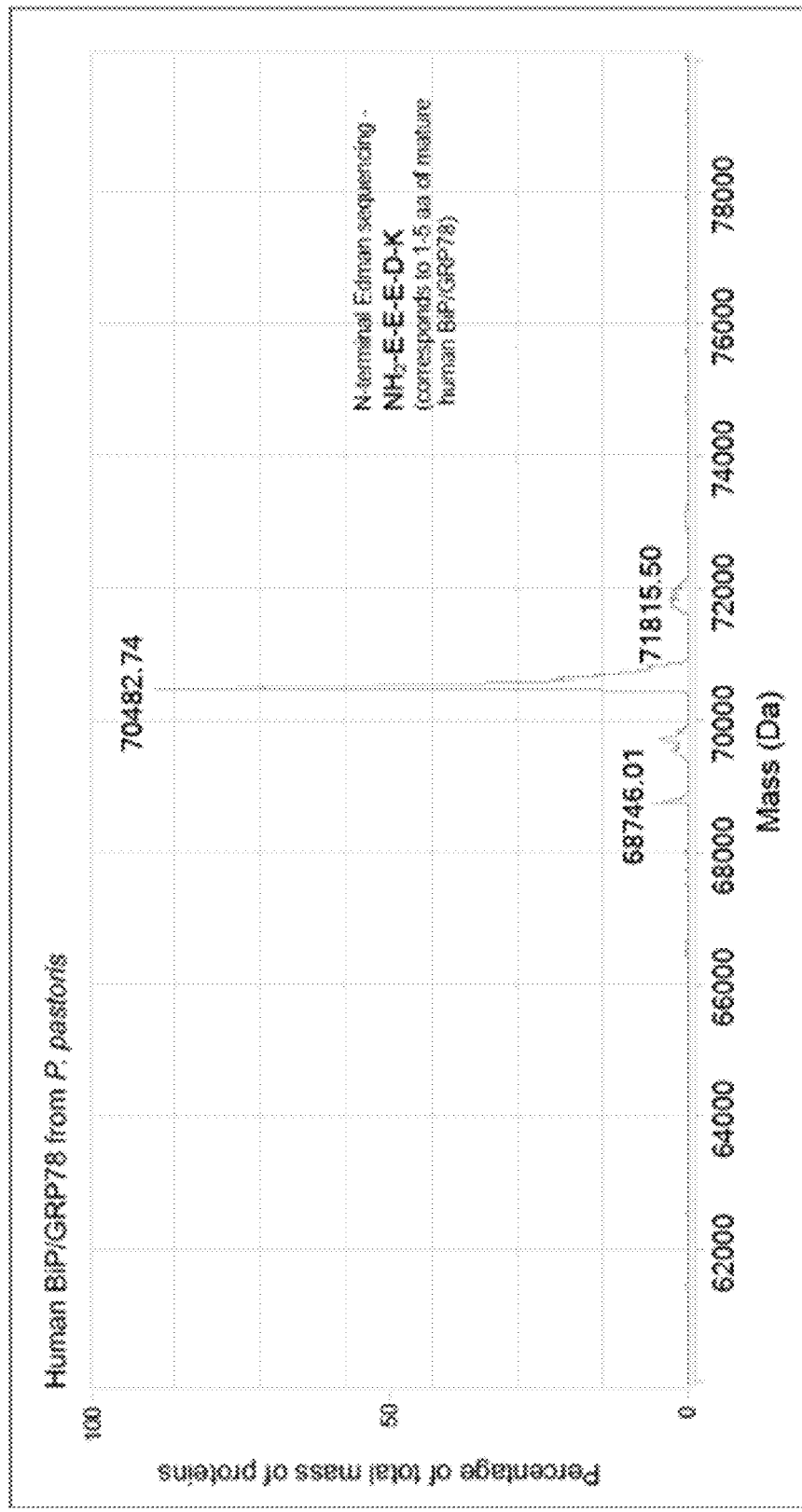

The band of purified secreted GRP78/BiP protein was excised from SDS-PAA gel and identified by trypsin digestion and MALDI-TOF/TOF tandemic MS/MS (mass spectrometry) together with UPLC/$MS^E$ method using a service of the Proteomics Centre at the Institute of Biochemistry (Vilnius, Lithuania). Tryptic peptide mass fingerprinting confirmed that purified secreted protein represents human GRP78/BiP, which was identified by both methods with a high level of confidence and ~57% sequence coverage (FIG. 5). FIG. 5 shows identified peptides (indicated in bold) of GRP78_HUMAN protein (Acc. No. P11021 in UniProt KB database). We were not able to identify N-terminal tryptic peptide by this method, which corresponds to N-terminal sequence of native mature GRP78/BiP from human cells. However, search in a UniProtKB database using PLGS (ProteinLynx Global Service) search engine in UPLC/MS$^E$ method identified a C-terminal human GRP78/BiP peptide (Y)GSAGPPPTGEEDTAEKDEL(-), which is underlined in FIG. 5. This demonstrated that secreted human BiP protein possesses intact C-terminal amino acid sequence including KDEL ER retention/retrieval signal. Further, the molecular mass of both S. cerevisiae- and P. pastoris-secreted BiP protein was measured by electrospray mass spectrometry (ESI-MS) using Agilent Q-TOF 6520 mass spectrometer. ESI-MS of a whole S. cerevisiae-derived recombinant GRP78/BiP protein molecule showed a molecular mass of ~70478 Da, which exactly corresponds to theoretically predicted mass of mature human GRP78/BiP (19-654 aa) (FIG. 6, upper panel). Whereas, P. pastoris-secreted BiP protein showed similar but slightly different molecular mass of 70482.74 Da (FIG. 6, lower panel), which was only 4 Da greater than the predicted mass of mature human GRP78/BiP (70478.57 Da). We suppose that this discrepancy may result from different buffers from which yeast-derived human BiP was taken for the analysis. In the case of S. cerevisiae-secreted BiP protein, we took a sample directly from ATPase buffer (50 mM HEPES, 50 mM NaCl, 2 mM $MgCl_2$, 5 mM ATP, pH 6.8), while P. pastoris-derived human GRP78/BiP was taken for the analysis from a BiP storage buffer (20 mM Tris-HCl, 350 mM NaCl, 0.5 mM DTT, 10% glycerol, pH 8.0) containing DTT. Possibly, increased molecular mass of P. pastoris-expressed BiP protein is determined by reduced cysteines in DTT containing sample.

Furthermore, N-terminal sequencing by Edman degradation confirmed that the first five N-terminal amino acids of the recombinant protein from both yeasts were $NH_2$-EEEDK (FIG. 6), which correspond the N-terminal sequence of mature human BiP protein after signal cleavage (Table 1). Taken together, these results indicated that native ER signal sequence of human BiP protein is recognized and correctly processed in yeast cells, and this allows translocation of recombinant protein into the ER following unexpected secretion outside the yeast cell. Also, the results proved that secreted human GRP78/BiP protein purified from the yeast cells does not carry any modifications.

GRP78/BiP protein produced in accord with the disclosed invention showed correct folding and activity of the product. Correct folding was assessed by partial proteolysis of recombinant BiP protein purified from S. cerevisiae and P. pastoris using a method described in Wei and Hendershot, 1995. The results are shown in FIG. 7 displaying partial proteolysis of BiP from S. cerevisiae (FIG. 7, panel A) and P. pastoris (FIG. 7, panel B): 5 µg of human BiP protein purified from yeast culture media was loaded onto each lane: 1—without proteinase; 2, 3 and 4—treated with 2 µg of proteinase K in the presence of 100 µM ATP (lanes 3) or 100 µM ADP (lanes 4) or in the absence of any of nucleotides (lanes 2). Reaction was performed in 65 µl volume in ATPase buffer (50 mM HEPES, pH=6.8, 50 mM NaCl, 2 mM $MgCl_2$) at 37° C. for 25 min., then stopped by adding 10 µl of 1 mg/ml PMSF and incubated on ice for 30 min. (according to Wei and Hendershot, 1995). Digested BiP protein was further analyzed by SDS-PAGE. M—molecular mass standards (Fermentas, Lithuania, SM0671). S. cerevi-siae-expressed BiP protein bound ATP, and this protected a ~60 kDa fragment from proteolysis by proteinase K, whereas binding of ADP protected ~44 kDa fragment (FIG. 7, panel A). Similar data was previously used to demonstrate correct folding of both native mammalian (Kassenbrock and Kelly, 1989) and E. coli-expressed recombinant BiP proteins (Wei and Hendershot, 1995).

For activity of yeast-expressed protein, an ATP-ase activity test of GRP78/BiP was used, also using an E. coli expressed analog as parallel control. The results are shown in FIG. 8. BiP protein produced in E. coli was purchased from Nordic BioSite (Cat. No. SPR-119), whereas yeast-expressed proteins were purified in this study. Reactions were performed in 50 µl volumes as follows: 1 µg of recombinant BiP protein (or equal volume of buffer for negative control) with 20 mM KCl and 20 µM ATP in ATPase buffer (50 mM HEPES, pH=6.8, 50 mM NaCl, 2 mM $MgCl_2$) was incubated at 25° C. for 75 min. Concentration of the phospate liberated from ATP was measured by spectrofotometer (TECAN Infinite® 200, wave length 620-650 nm) using Malachite Green Phosphate Assay Kit (Cayman Chemical) according to manufacturer' recommendations (detailed procedure of performed test is described in Bernal-Bayard et al., 2010). As it is shown in FIG. 8, there was three-fold higher yeast-expressed secreted BiP chaperone activity than that of commercial E. coli product (~6.3 µM versus ~2.1 µM of hydrolysed ATP by the same amount of protein in the same time). This considerable difference demonstrated an advantage of yeast-expressed products. ATP binding and protection of ~60 kDa domain of P. pastoris-derived BiP, as well as ~44 kDa fragment protected by ADP, was similar to that from S. cerevisiae-derived BiP (FIG. 7, panel B). The ATP-ase activity of P. pastoris-expressed BiP was also measured and showed similar results as for S. cerevisiae-expressed analog (FIG. 8, the average for P. pastoris-expressed BiP was slightly higher than for S. cerevisiae analog, but within the range of error) with about three fold increase compared to E. coli-expressed product.

Figure 9:
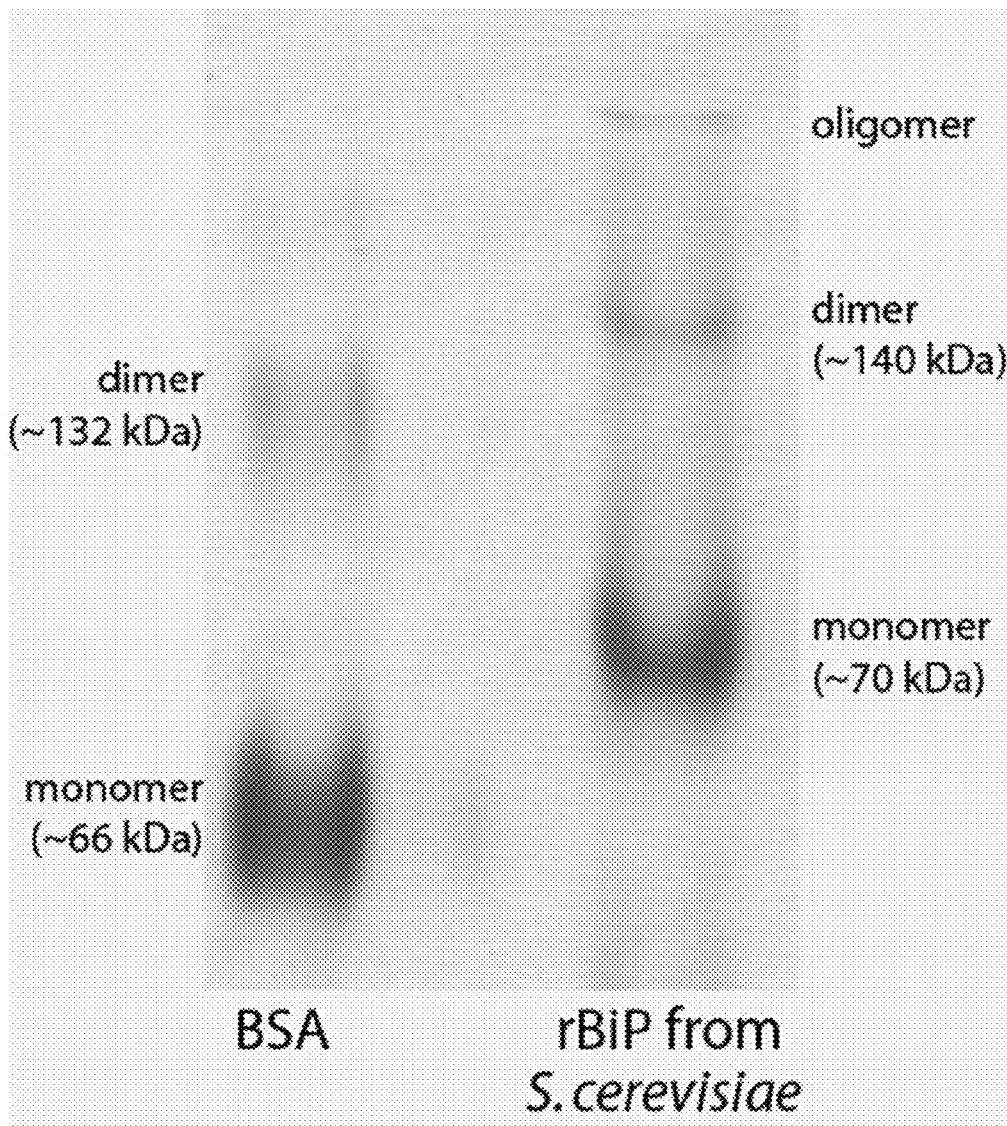
FIG. 9 shows native PAGE of recombinant human BiP protein purified from *S. cerevisiae*.

To explain such considerable difference in activity between yeast- and bacteria-expressed human BiP proteins we performed further experiments including test of BiP oligomerization by using native PAGE. Native PAGE procedure with yeast-expressed BiP protein was performed according to the protocol of Freiden et al., 1992, which was used for the assessment of the oligomerization of both native mammalian dog BiP (Freiden et al., 1992) and of E. coli-expressed hamster BiP protein (Wei and Hendershot, 1995). The native PAGE with S. cerevisiae-derived human BiP protein is shown in FIG. 9. 5 µg of human BiP protein purified from S. cerevisiae culture medium was loaded onto gel lane, whereas 5 µg of BSA was used as a molecular weight marker for the native PAGE. Observed approximate molecular weights are indicated in FIG. 9. Native PAGE of P. pastoris-derived human BiP is not shown, but it revealed very similar results. This test demonstrated that yeast-derived secreted human BiP protein is present in predominantly monomeric form. In mammalian cells BiP exists as both monomer and dimer (Freiden et al., 1992; Wei and Hendershot, 1995). In contrast, E. coli-expressed BiP protein was found mostly in dimeric form, although some monomers and higher order oligomers were also present (Blond-Elguindi et al., 1993; Wei and Hendershot, 1995). Therefore, these differences in oligomeric state might be related to different enzymatic activities of recombinant human BiP proteins. Moreover, yeast-expressed recombinant BiP protein undergoes protein quality control throughout the yeast secretion pathway; meanwhile E. coli-synthesized BiPs are purified by capturing all expressed BiP protein molecules independently of their folding state.

Example 2

Native Signal Peptide of Human Calreticulin Mediates Efficient Secretion of Correctly Processed Mature Recombinant Calreticulin in Yeast Growing amount of data associates calreticulin with many different functions in subcellular locations outside the ER. Analysis of protein functions requires substantial amounts of correctly folded, biologically active protein. In this study we introduce yeast *Saccharomyces cerevisiae* and *Pichia pastoris* as perfect hosts for production of human calreticulin. Our data demonstrate that native signal peptide of human calreticulin protein is recognized and correctly processed in the yeast cells, which leads to protein secretion. Secretion allows simple one-step purification of recombinant calreticulin protein from yeast culture medium with the yields exceeding 30 and 100 mg/L in *S. cerevisiae* and *P. pastoris*, respectively. Analysis of yeast-expressed secreted recombinant human calreticulin revealed that it possesses native amino acid sequence as in human cells and non-native modifications are not present in the recombinant product. Furthermore, limited proteolysis with trypsin suggested that yeast-derived calreticulin is correctly folded $Ca^{2+}$ binding protein. Finally, the recombinant secreted products appeared to be biologically active and induced cellular proliferation and migration of human fibroblasts in a wound healing scratch plate assay.

cDNA encoding full-length human calreticulin (Acc. no. M84739) was amplified from commercial human adult liver cDNA library (Clontech) by PCR using specific oligonucleotide primers CRTF (gta tct aga aca atg ctg cta tcc gtg ccg ttg) and CRTR (cag tct aga cta cag ctc gtc ctt ggc ctg), digested with restriction endonuclease (RE) XbaI and cloned into yeast expression vectors pFDC (Čiplys et al., 2011) and pPIC3.5K (Intvitrogen) into RE sites XbaI and AvrII under control of *S. cerevisiae* PGK1 or *P. pastoris* AOX1 promoters, respectively. Cloned CRT gene sequence (beginning from start codon ATG and ending with STOP codon TAG) was verified by DNA sequencing and generated plasmids pFDC-CRT and pPIC3.5K-CRT were used for transformation of yeast *S. cerevisiae* and *P. pastoris*, respectively. *S. cerevisiae* transformants were selected by resistance to formaldehyde and harboured multicopy autonomously replicating plasmid pFDC-CRT, whereas multicopy *P. pastoris* transformants were selected by resistance to G418 and strains with the most efficient secretion of CRT protein were chosen for further experiments. Both yeasts were used for expression of the full length CRT protein including native N-terminal signal peptide.

After expression of recombinant human calreticulin, cells were separated from the medium by centrifugation and yeast growth medium was further prefiltered with subsequent microfiltration of secreted protein through 0.2 μM filter. After microfiltration, proteins were concentrated and transferred into the binding buffer (20 mM Tris-HCl, pH 8.0) through tangential ultrafiltration using cassettes with 100 kDa cut-off membranes. Further, proteins were purified by ion-exchange chromatography on Sepharose Q. Such purification procedure was enough to reach up to 90% purity of secreted recombinant human calreticulin. Yields obtained were approx. 30 mg and 100 mg from 1 L culture medium in *S. cerevisiae* and *P. pastoris* expression systems, respectively.

Figure 10:
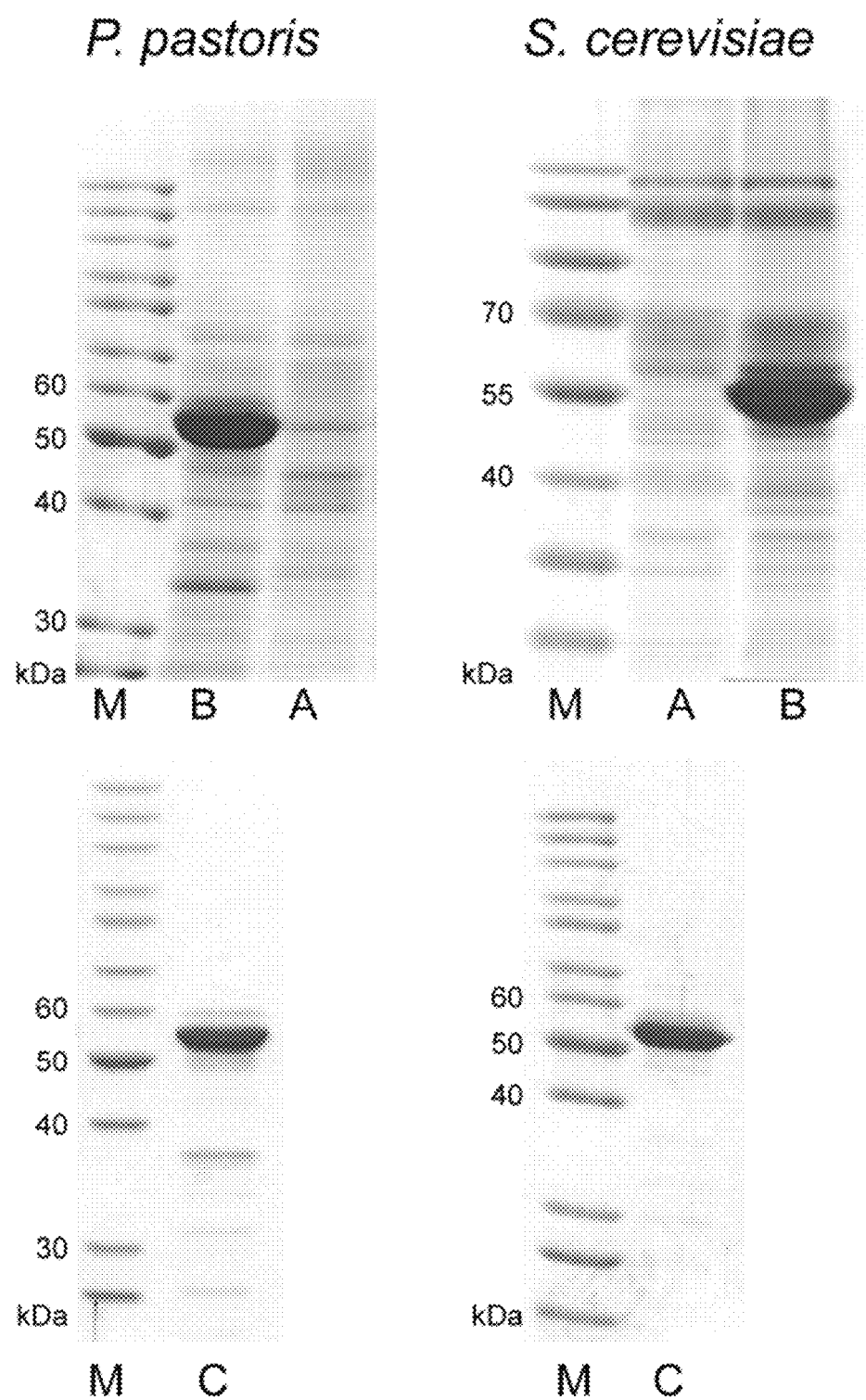
FIG. 10 shows SDS-PAGE analysis of yeast culture media and purified recombinant human calreticulin samples from *P. pastoris* and *S. cerevisiae*, respectively.

FIG. 10 shows SDS-PAGE analysis of yeast culture media and purified recombinant human calreticulin samples. Upper panel—yeast culture media after CRT expression in *P. pastoris* (10× concentrated medium supernatant) and *S. cerevisiae* (30× concentrated medium supernatant). A—media from control yeast strains without CRT gene; B—media from yeast strains expressing human CRT. Lower panel—purified secreted recombinant human CRT protein (C lanes). M—protein molecular weight markers.

Figure 11:
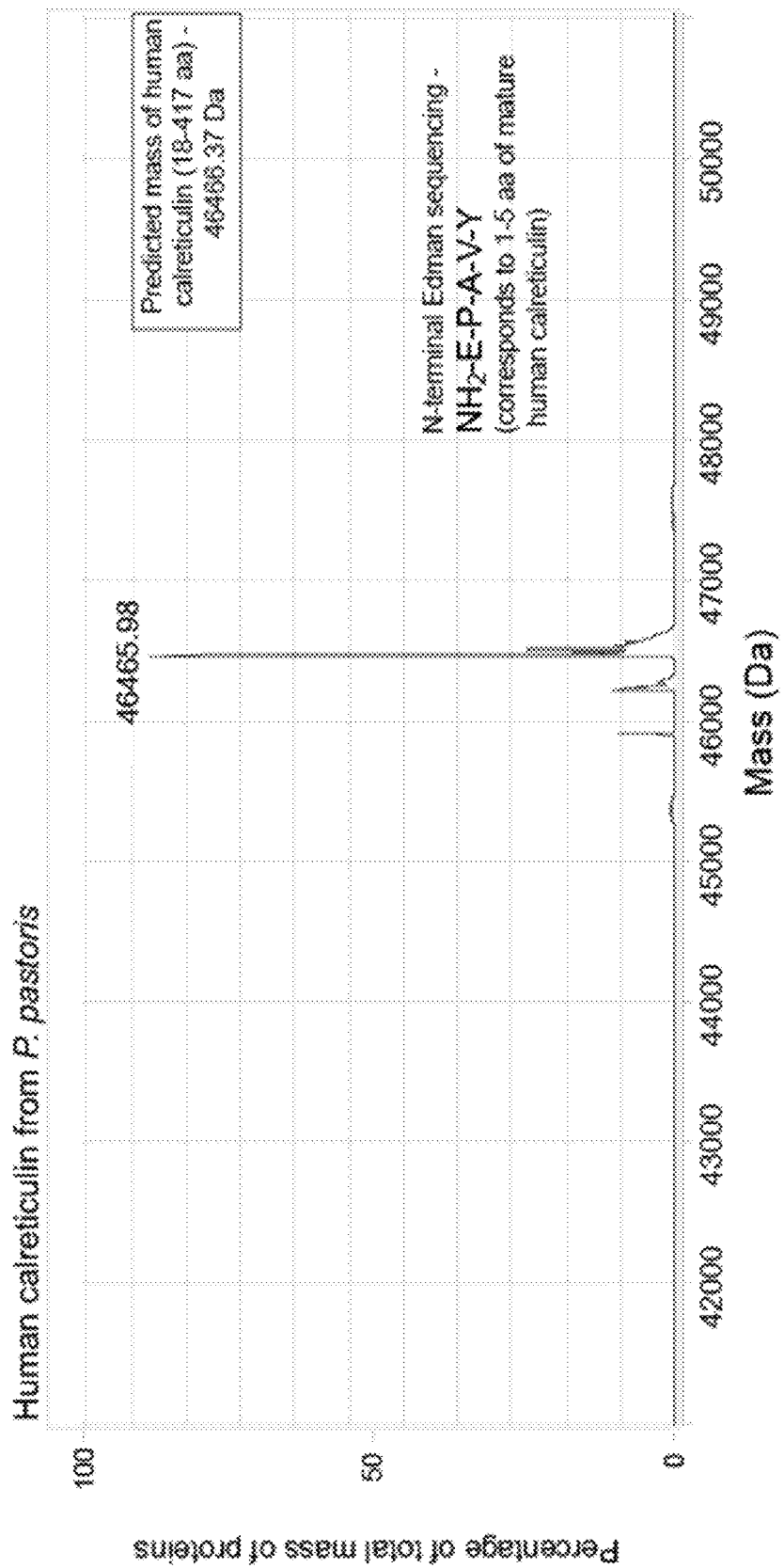
FIG. 11 shows tryptic peptide mass fingerprinting of *S. cerevisiae*-expressed protein, which confirmed that purified secreted protein represents human calreticulin with correctly processed N-terminal amino acid sequence.
Figure 12:
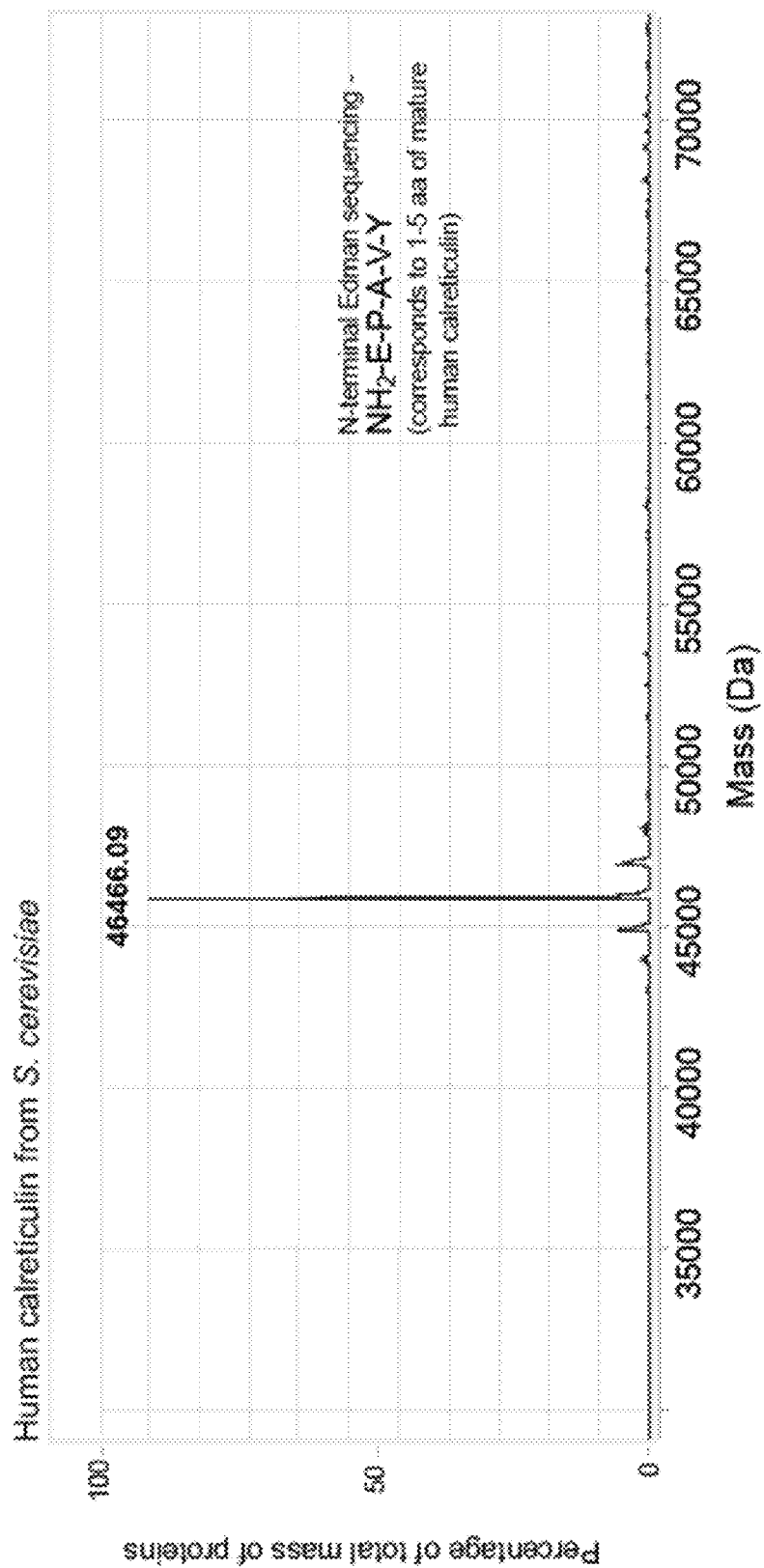
FIG. 12 shows ESI-MS and N-terminal Edman sequencing of secreted recombinant human calreticulin purified from *P. pastoris* and *S. cerevisiae*.

Tryptic peptide mass fingerprinting confirmed that purified secreted protein represents human calreticulin (FIG. 11, identified peptides are indicated in bold). Moreover, N-terminal tryptic peptide (EPAVYFK) was identified, which corresponds to N-terminal sequence of native mature calreticulin from human cells. Further, an important result was obtained by ESI-MS of a whole yeast-derived recombinant calreticulin protein molecule. Both *P. pastoris*- and *S. cerevisiae*-secreted CRT protein showed a molecular mass of ~46466 Da, which exactly corresponds to theoretically predicted mass of mature human CRT (18-417 aa) (FIG. 12). Furthermore, N-terminal sequencing by Edman degradation confirmed that the first five N-terminal amino acids of the recombinant protein from both yeasts were $NH_2$-EPAVY, which corresponds the N-terminal sequence of mature human CRT protein after signal cleavage. Taken together, these results indicated that native ER signal sequence of human CRT protein is recognized and correctly processed in yeast cells, and this allows translocation of recombinant protein into the ER following unexpected secretion outside the yeast cell. Also, the results proved that secreted human calreticulin purified from yeast cells does not carry any modification.

Figure 13:
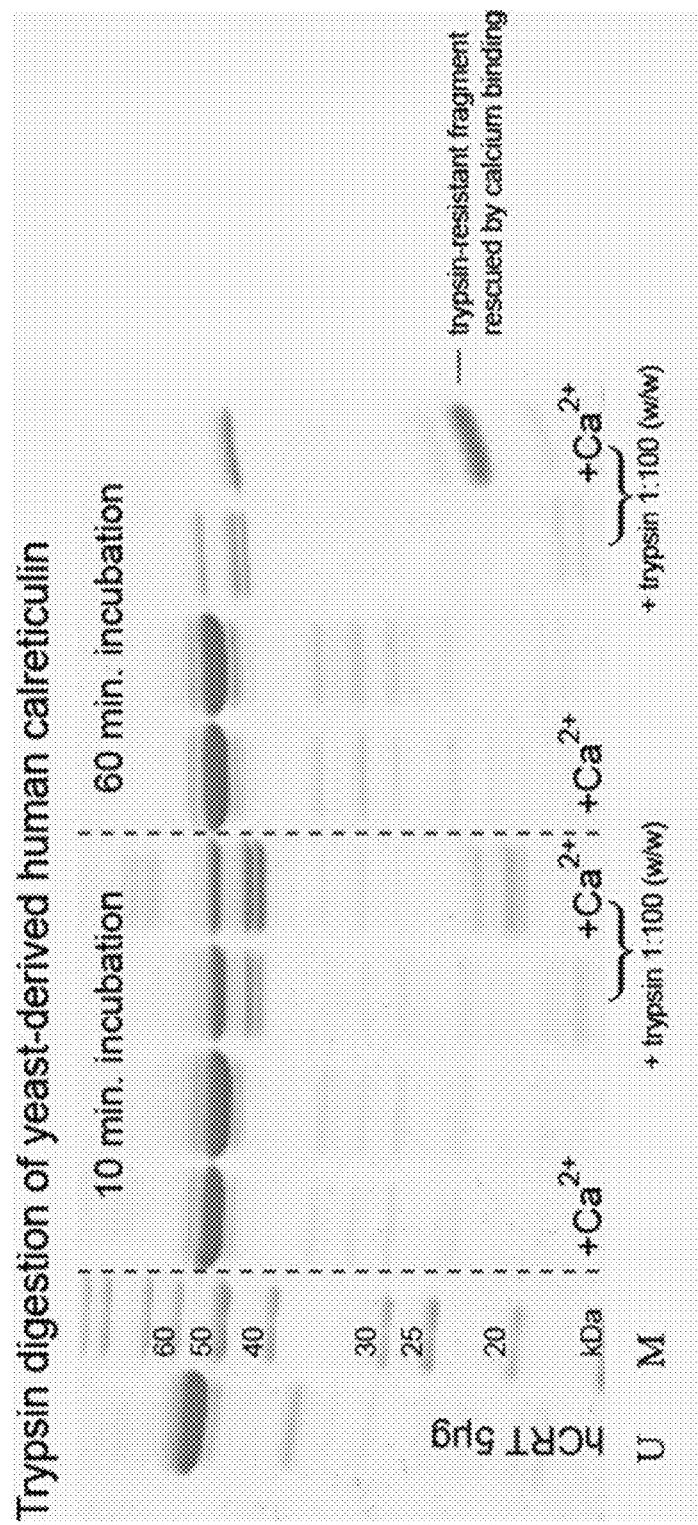
FIG. 13 shows trypsin digestion of recombinant human calreticulin purified from *P. pastoris* culture medium that confirms correct folding of yeast-secreted human protein.

Partial digestion of calreticulin with trypsin (according to Corbett et al., 2000, *Eur J Biochem.* 268:2558-65; Højrup et al., 2001, *J Biol Chem.* 275:27177-85) was used to show correct folding and $Ca^{2+}$ binding of yeast-expressed hCRT. hCRT was diluted to 1 mg/ml concentration in storage buffer containing 3 mM $CaCl_2$. Digestion was performed in 50 μl volume by adding 1 μl of 0.5 mg/ml trypsin (ratio of hCRT:trypsin was 100:1 (w/w)). In a control tube, calcium was removed by adding EDTA to 5 mM concentration. Controls without trypsin and EDTA were also used. The reaction was stopped after two time points, 10 min. and 60 min., by adding 1 mM PMSF. The samples were boiled, loaded onto the gels, and SDS-PAGE was performed. The results are shown in FIG. 13: Trypsin digestion of recombinant human calreticulin purified from *P. pastoris* culture medium. U— Untreated sample with 5 μg of hCRT, incubated at 37° C. without calcium and EDTA; For other samples reaction was performed at 37° C. in storage buffer (20 mM Tris-HCl, pH 7.5, 100 mM NaCl, 3 mM $CaCl_2$). In the control tubes calcium was removed by addition of 5 mM EDTA. M—protein molecular weight marker ("Page Ruler Unstained protein ladder", Fermentas, #26614). Analysis of *S. cerevisiae*-derived CRT is not shown, but the same results were obtained.

Digestion with trypsin revealed two CRT bands resistant to protease digestion—about 50 kDa and about 23 kDa, respectively. Partial digestion of human placental CRT with trypsin to ~50 kDa fragment was reported earlier by Højrup et al., 2001. Moreover, they reported that addition of $Ca^{2+}$ increases proteolysis rate of native CRT. We also observed this effect (FIG. 13; compare hCRT samples with and without calcium after trypsin digestion). However, addition of calcium resulted in the resistance of ~23 kDa fragment of yeast-expressed hCRT to trypsin digestion (FIG. 13). It is in accordance with the data reported for rabbit CRT expressed in *P. pastoris*, as after calcium binding ~27 kDa similar CRT band was also resistant to protease digestion (Corbett et al., 2000). Limited proteolysis with trypsin is regarded as the best test for the quality of recombinant calreticulin and is used for analysis of commercial CRT products (Abcam, ab15729, see "Properties"). Therefore, limited digestion with trypsin suggested that yeast-expressed human CRT is correctly folded $Ca^{2+}$ binding protein and has similar properties to native human placental CRT (Højrup et al., 2001) and recombinant rabbit CRT expressed in *P. pastoris* (Corbett et al., 2000).

After demonstration of correct folding and calcium-binding properties of yeast-expressed hCRT, we have assessed biological activity of both *P. pastoris*- and *S. cerevisiae*-expressed human recombinant protein products. It was previously shown that recombinant human calreticulin expressed in bacteria *E. coli* improves wound healing in both murine and porcine animal models through multiple biological effects (Gold et al., 2006; Nanney et al., 2008; Gold et al., 2010; Greives et al., 2012). Therefore, it was especially important to compare *E. coli*- and yeast-expressed hCRTs in a parallel test of biological activity that directly relates to reported wound healing effects. For cellular proliferation and migration assays here we used the same human CRT from bacteria that was earlier shown to improve wound healing in vivo by causing a dose-dependent increase in epithelial migration and granulation tissue formation in both murine and porcine normal and impaired animal models of skin injury (Gold et al., 2006; Greives et al., 2012). Yeast-expressed hCRT proteins were tested in parallel with recombinant hCRT from bacteria (from M. Michalak, University of Alberta, Edmonton Alberta, Canada). In vitro assay for cellular proliferation was performed according to Nanney et al., 2008; and Greives et al., 2012. Briefly, human fibroblasts were seeded at 1,000 cells per well in 96 well plates and grown to 50% confluency. After 24 hours starvation in 0.5% FBS media, treatment was applied in 0.5% media for 24 hours. Cells were then incubated in MTS solution for 1 hour and absorbance was measured at 490 nm. Both *S. cerevisiae*- and *P. pastoris*-expressed human calreticulin showed significantly higher induction of human fibroblast proliferation compared to the same protein purified from bacteria *E. coli* (Table 2 and FIG. 14). This may be explained by the fact that yeast-secreted hCRT must undergo thorough protein quality control throughout the yeast secretion pathway, which allows secretion of correctly folded proteins only; meanwhile *E. coli*-synthesized analog is purified by capturing all expressed hCRT molecules independently of their folding state.

TABLE 2

Cellular proliferation of human fibroblasts induced by hCRT expressed in bacteria, *S. cerevisiae* and *P. pastoris*, respectively.

|  | | Trial 1 Fold Change | Trial 2 Fold Change | Trial 3 Fold Change | Trial 4 Fold Change | Trial 5 Fold Change | Trial 6 Fold Change | Average | Error |
|---|---|---|---|---|---|---|---|---|---|
| Human CRT (Bacteria) | ng/mL | | | | | | | | |
| | 0 | 1 | 1 | 1 | 1 | 1 | 1 | 1 | 0.016294195 |
| | 0.1 | 1.133514986 | 1.259426848 | 1.103481625 | 0.989879823 | 1.158415842 | 1.325415677 | 1.161689133 | 0.024683693 |
| | 1 | 1.253405995 | 1.274509804 | 1.077369439 | 1.12397217 | 1.121287129 | 1.375296912 | 1.204306908 | 0.03343521 |
| | 10 | 1.389645777 | 1.273001508 | 1.138297872 | 1.064516129 | 1.193069307 | 1.472684086 | 1.255202446 | 0.021668366 |
| | 100 | 1.234332425 | 1.021116139 | 1.151837524 | 1.144212524 | 1.08539604 | 1.344418052 | 1.163552117 | 0.020869458 |
| | 10% FBS | 1.667574932 | 1.684766214 | 1.586073501 | 1.442125237 | 1.522277228 | 1.714964371 | 1.60296358 | 0.013341821 |
| Human CRT (*S. cerevisiae*) | 0.1 | 1.495912807 | 1.455505279 | 1.147001934 | 1.154965212 | 1.274752475 | 1.356294537 | 1.314072041 | 0.011533147 |
| | 1 | 1.659400545 | 1.395173454 | 1.261121857 | 1.18342821 | 1.103960396 | 1.448931116 | 1.342002596 | 0.030760373 |
| | 10 | 1.613079019 | 1.375565611 | 1.211798839 | 1.275142315 | 1.245049505 | 1.51543943 | 1.37267912 | 0.023089937 |
| | 100 | 1.286103542 | 1.027149321 | 1.131528046 | 1.212523719 | 1.183168317 | 1.410926366 | 1.208566552 | 0.015389875 |
| Human CRT (*P. pastoris*) | 0.1 | 1.008174387 | 1.562594268 | 1.091876209 | 1.201771031 | 1.056930693 | 1.368171021 | 1.214919602 | 0.019008118 |
| | 1 | 1.177111717 | 1.358974359 | 1.282398453 | 1.216951297 | 1.128712871 | 1.337292162 | 1.250240143 | 0.022952194 |
| | 10 | 1.29972752 | 1.524886878 | 1.235976789 | 1.187223276 | 1.180693069 | 1.622327791 | 1.341805887 | 0.019054 |
| | 100 | 1.525885559 | 1.075414781 | 1.132495164 | 1.156862745 | 1.091584158 | 1.358669834 | 1.223485374 | 0.013052392 |

Figure 14:
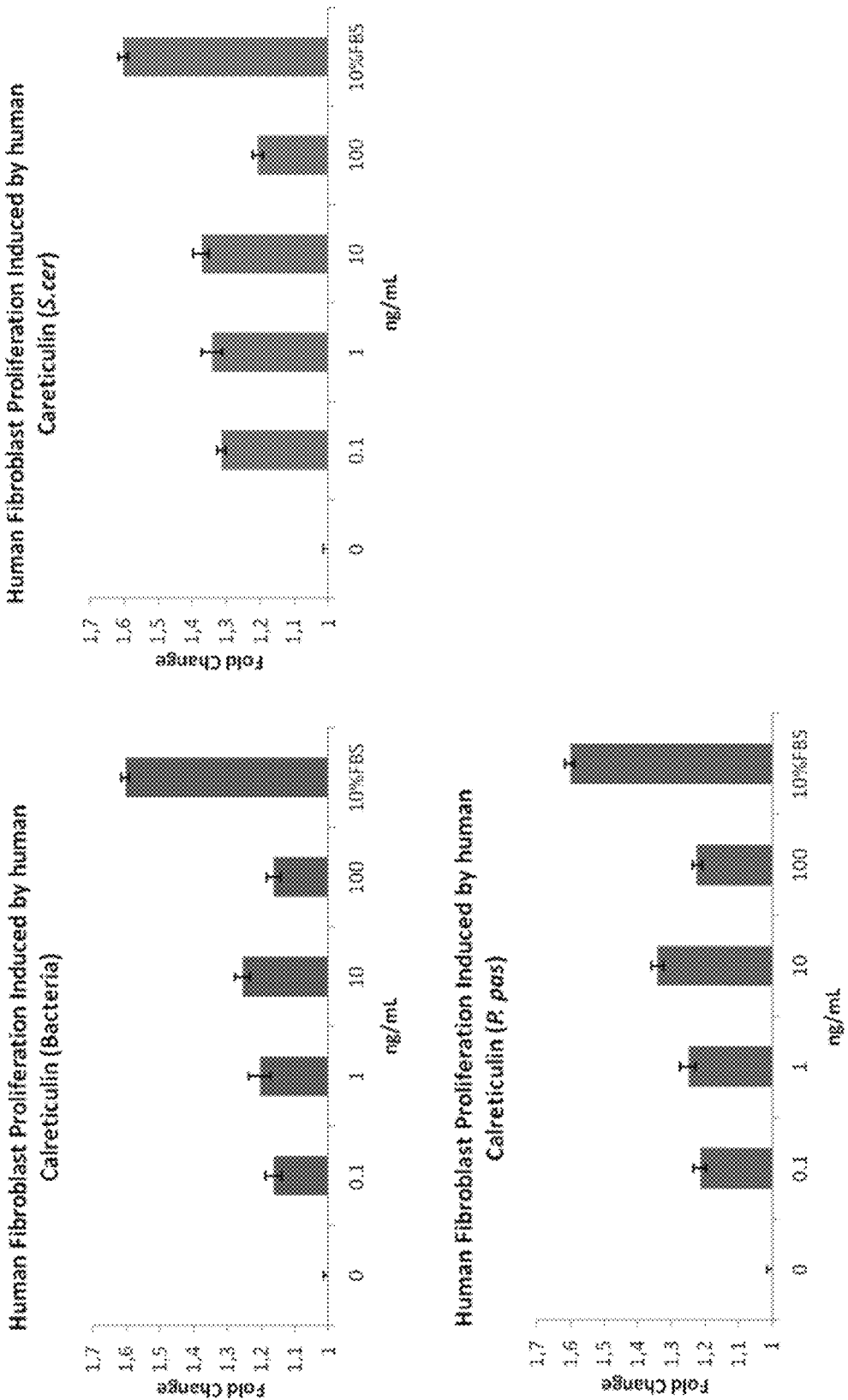
FIG. 14 shows data on human fibroblast proliferation induced by recombinant calreticulin proteins derived from bacteria and yeasts.

Note: graphical view of the results is shown in FIG. 14.

Another biological hCRT activity test was wound healing scratch plate assay (Nanney et al., 2008; Greives et. al., 2012). Human fibroblasts were seeded at 10,000 cells per well in 24 well plates and grown to 80% confluency. After 24 hour starvation in 0.5% FBS media, a scratch was made in the middle of the well with a 200 µl pipet tip. Treatment was applied in 0.5% FBS media. Pictures were taken at 0 hours and 6 hours. Results showed that the average for *E. coli*-expressed hCRT induction of human fibroblast migration was slightly higher than for yeast-derived analogues, but within the range of error (Table 3 and FIG. 15). Both bacteria- and yeast-expressed hCRT showed significantly higher induction of cellular migration, than negative (0.5% FBS—Fetal Bovine Serum) and positive (10% FBS) controls, respectively. It may be concluded that yeast-expressed recombinant hCRT is biologically active and induces migration of human fibroblasts at the similar extent as hCRT analog from bacteria.

TABLE 3

Cellular migration of human fibroblasts induced by hCRT expressed in bacteria, *S. cerevisiae* and *P. pastoris*, respectively.

| Treatment | ng/mL | Percent migration Trial 1 | Percent migration Trial 2 | Average | Error |
|---|---|---|---|---|---|
| 0.5% FBS | | 5.378067 | 5.60535 | 5.491708 | 1.144876 |
| 10% FBS | | 7.41555 | 6.80745 | 7.1115 | 0.733128 |
| Human CRT (Bacteria) | 1 | 9.2857 | 8.4337 | 8.8597 | 0.710761 |
| | 10 | 8.03795 | 10.625 | 9.331475 | 1.203801 |
| | 100 | 6.62775 | 8.590067 | 7.608908 | 0.421805 |
| Human CRT (*S. cerevisiae*) | 1 | 8.203467 | 5.88745 | 7.045458 | 0.729564 |
| | 10 | 6.90875 | 8.869667 | 7.889208 | 0.832518 |
| | 100 | 9.46755 | 7.8812 | 8.674375 | 0.696941 |
| Human CRT (*P. pastoris*) | 1 | 8.24245 | 8.02525 | 8.13385 | 0.988465 |
| | 10 | 8.79435 | 8.6602 | 8.727275 | 0.342841 |
| | 100 | 8.0294 | 6.91955 | 7.474475 | 0.800834 |

Figure 15:
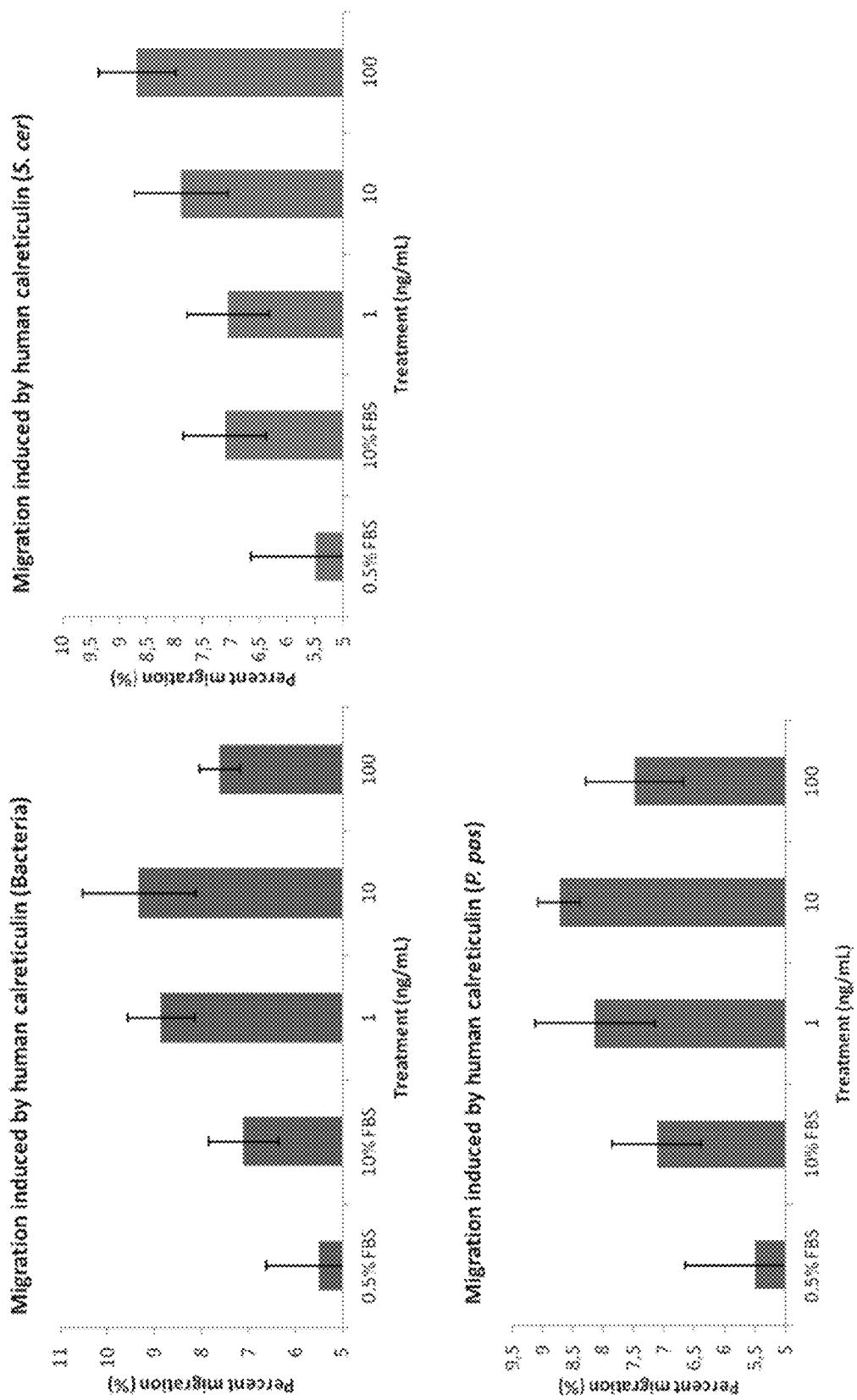
FIG. 15 shows data of wound healing scratch plate assay. Human fibroblast migration was induced by recombinant calreticulin proteins derived from bacteria or yeasts.

Note: graphical view of the results is shown in FIG. 15.

Taken together, here we demonstrate that the native signal of human calreticulin is correctly cleaved and drives secretion in yeast cells. Sequence of yeast-secreted human calreticulin fully corresponds to mature protein from human cells, and protein is free of yeast-derived modifications. Therefore, yeast cells are excellent host for production of large amounts of correctly folded native recombinant human calreticulin.

Example 3

Native Signal Peptide of Human ERp57 Disulfide Isomerase Mediates Secretion of Active Native Recombinant ERp57 Protein in Yeast *Saccharomyces cerevisiae* and *Pichia pastoris*

Human ERp57 protein is mainly glycoprotein specific disulfide isomerase, which facilitates folding of glycoprotein precursors in the ER in the concert with ER lectin chaperones calreticulin and calnexin.

A growing amount of data also associates ERp57 protein with many different functions in other subcellular locations outside the ER. Those functions are often not well understood and require further studies and deeper analysis. Analysis of protein functions generally requires relatively large amounts of biologically active protein, which as much as possible resembles its native state.

Yeast *Saccharomyces cerevisiae* were introduced as a perfect host for production of human ERp57 protein. We found that endogenous signal peptide of human ERp57 protein was recognized and correctly processed in yeast cells, which subsequently leads to the secretion of the ERp57 protein. Secreted recombinant ERp57 protein possessed native amino acid sequence and was biologically active. Moreover, secretion allowed simple one-step purification of native recombinant human ERp57 protein, with yields up to 10 mg/L.

This example shows that native signal peptide of human ERp57 was correctly processed in *S. cerevisiae*, that native sequence human ERp57 was secreted in yeast *S. cerevisiae*, and that secreted native recombinant human ERp57 was biologically active.

Enzymes and kits for DNA manipulations were from ThermoScientific. Primers were from IDT.

For plasmids, strains, media, yeast transformation and cultivation, all DNA manipulations were performed according to standard procedures (Sambrook and Russell, 2001). Bacterial recombinants were screened in *Escherichia coli* DH5αF' cells. The yeast *S. cerevisiae* strain AH22 MATa leu2 his4 was used for expression experiments. Transformation of *S. cerevisiae* cells was performed by conventional methods (Sambrook and Russell, 2001). The selection of transformants resistant to formaldehyde was carried out on YEPD (yeast extract 1%, peptone 2%, dextrose 2%) agar supplemented with 4 mM formaldehyde. *S. cerevisiae* transformants were grown in YEPD medium supplemented with 4 mM formaldehyde.

For protein expression and purification, yeast cells carrying the human PDIA3 gene were grown for 36 h in YEPD medium. Cells were separated from the medium by centrifugation at 2000×g for 10 min. Yeast growth medium was further prefiltered through qualitative filter paper (VWR, cat. no. 516-0812) with subsequent microfiltration through 1.6 μM (SartoriusStedim Biotech, cat. no. FT-3-1101-047), 0.45 μM (SartoriusStedim Biotech, cat. no. 15406-47) and 0.2 μM (SartoriusStedim Biotech, cat. no. 15407-47-MIN) filters. After microfiltration, proteins from the medium were concentrated and transferred into the binding buffer (20 mM Tris-HCl, pH 8.0) through tangential ultrafiltration using cassettes with 50 kDa cut-off membranes (SartoriusStedim Biotech, cat. no. VF20P3). Proteins were incubated for 30 min with heparin sepharose (GE Healthcare, cat. no. 17-0998-01) in batch format. Unbound proteins were removed while bound proteins were eluted with a step NaCl gradient (150 mM—250 mM—350 mM). Elution fractions were analyzed by SDS-PAGE. All showed more than 90% pure human ERp57 protein. All fractions were pooled and dialysed against 20 mM Tris-HCl, pH 8.0 NaCl 100 mM buffer.

Insulin turbidity assay was performed as described (Hirano et al., 1995; Frickel et al., 2004). The assay mixture was prepared in a cuvette by addition of 50 μl insulin (Sigma-Aldrich, cat. no. 12643) (1 mg/ml in 100 mM potassium acetate pH 7.5, 2 mM EDTA) plus tested protein and water for a final volume of 60 μl. The reaction was started by pipetting 2 μl dithiothreitol (10 mM) in a cuvette. The cuvette was then thoroughly mixed and placed in the spectrophotometer (Tecan's Infinite M200). Measurements were performed at 650 nm using 60-s recordings. Assays lasting up to 60 min were not mixed further. The onset of aggregation was defined as the time where OD650 had reached the value of 0.025. The enzyme concentration at which this occurred was plotted against the onset of aggregation in order to obtain a concentration-dependent activity curve for the reductase activity of each oxidoreductase. *E. coli* thioredoxin was purchased from Sigma-Aldrich (cat. no. T0910) and recombinant human ERp57, produced in *E. coli*, was purchased from Nordic BioSite (cat. no. PAT-80438-1) were used as controls.

N terminus sequencing of yeast secreted human ERp57 protein by Edman degradation was performed by AltaBioscience. The molecular mass of protein was measured by electrospray mass spectrometry using Agilent Q-TOF 6520 mass spectrometer. Protein concentrations were determined by Roti-Nanoquant Protein-assay (Carl Roth Gmbh., cat. no. K880).

Densitometric analysis of SDS-PAGE gels, scanned with ImageSanner III (GE Healthcare) were performed with ImageQuant TL (GE Healthcare) software using default settings.

Precipitation of proteins from yeast growth medium for SDS-PAGE analysis was performed based on a defined methanol-chloroform-water mixture as described (Wessel and Flügge, 1984).

Figure 16:
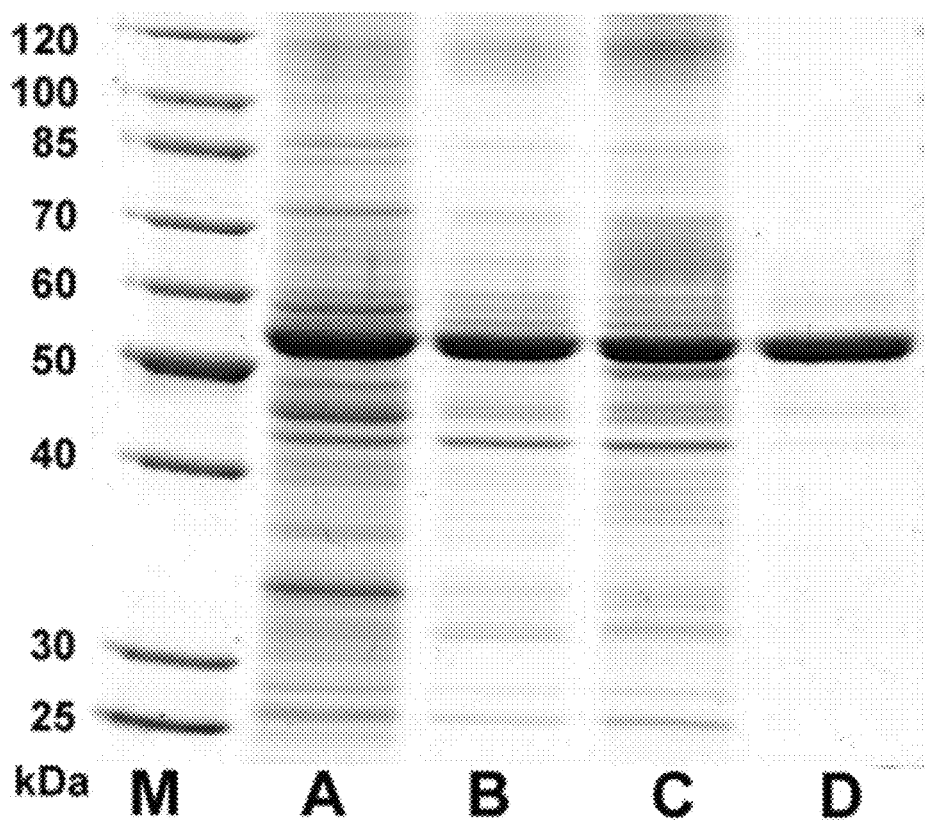
FIG. 16 shows purification of secreted recombinant human ERp57 protein from yeast culture medium. Lanes represent protein molecular weight markers (M), crude yeast growth medium after human ERp57 expression in *S. cerevisiae* (A), the same yeast growth medium after microfiltration (B), the same medium after tangential ultrafiltration (C) and secreted recombinant human ERp57 protein purified from the same medium by one-step affinity chromatography using heparin Sepharose (D).

For construction of human ERp57 yeast expression vector, ERp57 coding gene (PDIA3, Acc. no. U42068) was cloned under constitutive yeast PGK1 promoter in pFDC vector, yielding pFDC-hERp57 plasmid as it was described previously (Čiplys et al., 2011). Briefly, human PDIA3 gene was cloned from human adult liver cDNA library (Clontech) using primers that generate XbaI restriction sites on both ends of the gene, allowing restriction cloning into the XbaI site of pFDC vector between yeast PGK1 promoter and terminator. Yeast expression vector pFDC-hERp57 was transformed into the *S. cerevisiae* strain AH22. Yeast cells harboring human PDIA3 gene were grown in YEPD medium and secreted native recombinant human ERp57 protein was purified to 90% purity as described above. The purification procedure is illustrated in FIG. 16: A—crude yeast growth medium (20× concentrated), B—yeast growth medium after microfiltration (20× concentrated), C—20× concentrated proteins from yeast growth medium in binding buffer after tangential ultrafiltration; D—purified yeast-derived recombinant human ERp57 protein (2 μg), M—unstained protein ladder (ThermoScientific, cat. No. 26614). According to data obtained from densitometric analysis of SDS-PAGE gels, secreted human ERp57 protein constitutes for approx. 30% of all yeast secreted protein (FIG. 16 lane A), subsequent microfiltration increases its purity to approx. 50% (FIG. 16 lane B) and one-step affinity chromatography using heparin Sepharose is enough to reach over 90% purity (FIG. 16 lane D). Yields obtained were approx. 9 mg from 1 L culture medium with purification efficiency reaching up to 90%. In summary, secretion of human ERp57 into the yeast growth medium allows simple and cost-effective purification of native recombinant protein.

N-terminal sequencing by Edman degradation was performed for identification and characterization of purified secreted protein. The first five N-terminal amino acids of the recombinant protein were $NH_2$—SDVLE, which corresponds the N-terminal sequence of mature human ERp57 protein after signal cleavage (Charnock-Jones et al., 1996). These results indicate that native ER signal sequence of human ERp57 protein is recognized and correctly processed in yeast cells, and this allows translocation of recombinant protein into the ER following unexpected secretion outside the yeast cell. *S. cerevisiae* alpha-mating factor signal sequence is usually employed for secretion of recombinant proteins in yeast, since native secretion signals are rarely effective (Sleep et al., 1990; Ferrarese et al., 1998; Guo and Ma, 2008), even though usage of native secretion signals offers several advantages. First of all, it simplifies the cloning of the gene, and, most importantly, it allows secretion of recombinant protein without any additional amino acids, as the disclosed data illustrate. In contrast, some additional amino acids are usually introduced into recombinant product when using non-native signal sequences (Andrin et al., 2000).

Figure 17:
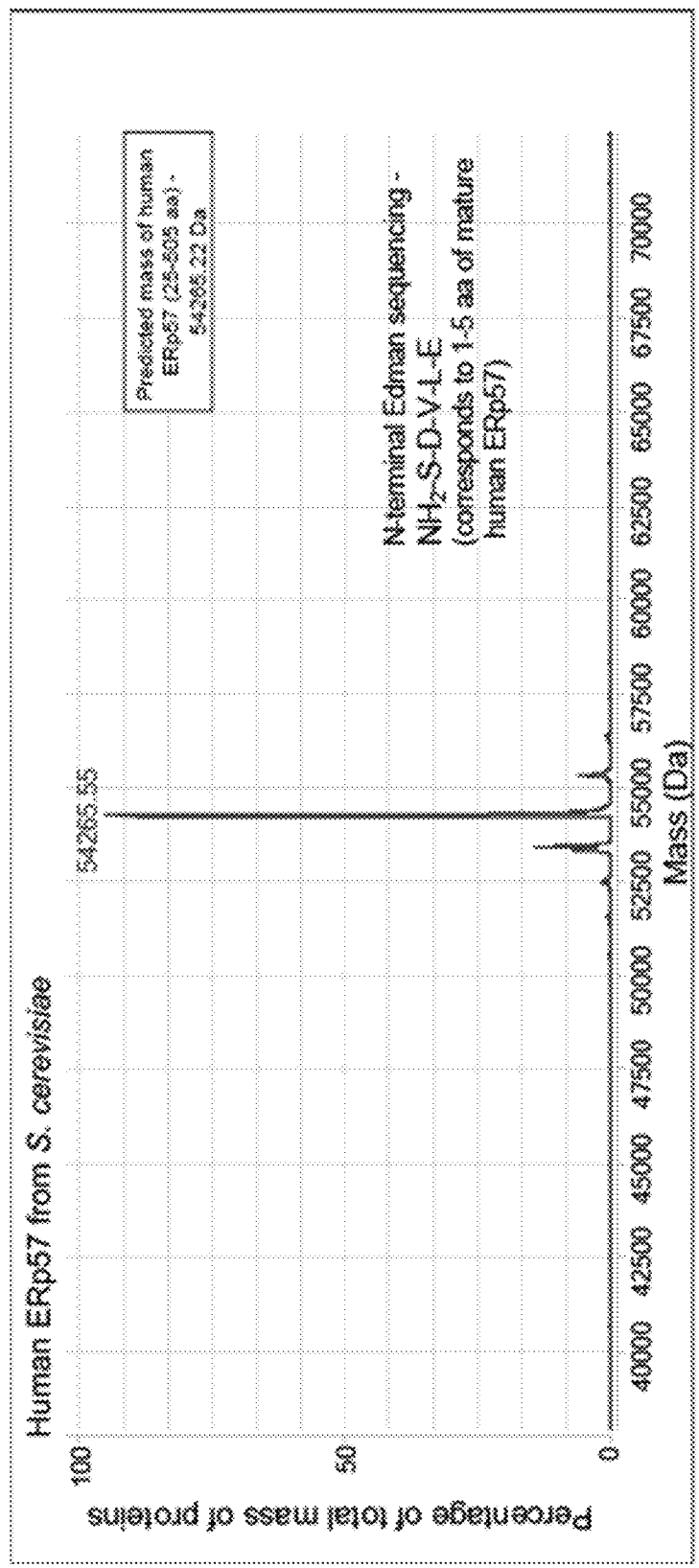
FIG. 17 shows ESI-MS and N-terminal Edman sequencing of secreted recombinant human ERp57 purified from *S. cerevisiae*.
Figure 18:
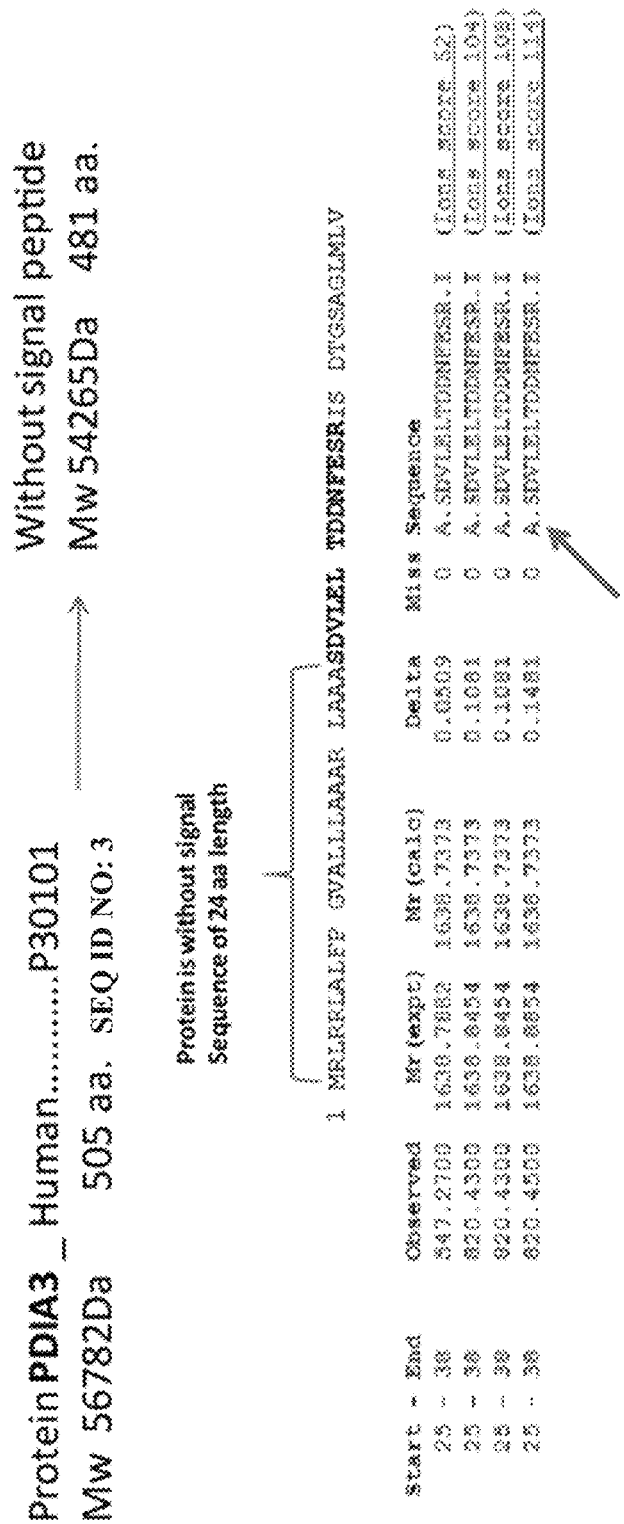
FIG. 18 shows identification of protein N-terminus by tryptic peptide mass fingerprinting of secreted recombinant human chaperone ERp57 (PDIA3) purified from *S. cerevisiae*.

Mass spectrometry results of yeast-derived purified human ERp57 protein showed the mass of 54265.55 Daltons, which exactly corresponds to theoretically predicted mass of mature human ERp57 (25-505 aa) (FIG. 17). It indicates two things: (a) recombinant human ERp57 protein is exactly the same polypeptide as mature human ERp57 (including predicted ER retention signal QEDL on the C terminus of the protein) and (b) it has no yeast-derived modifications—a very important characteristic for recombinant proteins. Moreover, mass spectroscopy analysis revealed that the protein was highly pure (FIG. 17). In addition, we performed tryptic peptide mass fingerprint analysis of *S. cerevisiae*-purified recombinant secreted ERp57 and have identified N-terminal peptide SDVLELTDDNFESR (FIG. 18, indicated in bold), which corresponds to the N-terminus of mature human ERp57 protein, identified in a database search as PDIA3_Human (Acc. No. P30101). Together with N-terminal sequencing and ESI-MS data this once more demonstrates correct processing of the secreted recombinant human ERp57 protein product.

The presence of intact QEDL sequence in recombinant human ERp57, which usually serves as ER retention signal in human cells, raises question about reasons of secretion of human protein by yeast cells and about retention of proteins in the ER in general. In some cases ERp57 was found on the surface of the human cells, and this suggests several important functions for the protein (Turano et al., 2011). Secretion of human ERp57 protein by *S. cerevisiae* cells could be explained by yeast preference for the HDEL rather than QDEL signal for the retrieval of ER-residing proteins (Dean and Pelham, 1990), but it is not the reason in this case, because replacement of QEDL with the HDEL sequence did not suppress the secretion of ERp57 (our unpublished data).

Also, overload of the yeast ER retrieval machinery can be omitted as the reason for secretion of human ERp57, because overexpression of yeast KAR2 protein with native HDEL ER retrieval sequence using the same pFDC vector did not lead to the secretion of this protein (our unpublished data). Moreover, human PDI, which is homologue of human ERp57 and yeast PDI proteins and contains KDEL ER retrieval sequence, was also expressed using the same pFDC vector, and in this case secretion of recombinant protein was not observed (our unpublished data). These experiments indicate that retention of ER luminal proteins is complicated and still unsolved mechanism, which does not strictly depend on HDEL/KDEL retrieval mechanism. Our finding, secretion of human ERp57 by yeast cells, could serve as a convenient model for studying this phenomenon.

Activity of yeast derived recombinant human ERp57 protein was measured by an insulin turbidity test that is often used for characterization of protein disulfide isomerases (Hirano et al., 1995; Antoniou et al., 2000; Frickel et al., 2004; Celli and Jaiswal, 2003). Recombinant ERp57 exhibited thiol-dependent reductase activity which catalyzes the reduction of insulin disulfides by dithiothreitol (FIG. 19). Reductase activity of the protein was compared to *E. coli* thioredoxin and commercially available *E. coli*-derived recombinant human ERp57. Thiol-dependent catalytic activity of yeast-derived recombinant human ERp57 protein assayed using the insulin precipitation method is shown in FIG. 19: Various concentrations of *E. coli* thioredoxin (♦), purified *S. cerevisiae* secreted human recombinant ERp57 (■) and human recombinant ERp57 purified from *E. coli* (▲) were tested for their ability to catalyze the reduction of 130 mM insulin by 0.33 mM DTT. The onset of aggregation was defined as the time when the optical density at 650 nm had reached a value of 0.025 and was plotted against the concentration of catalyst used. Data are the average of three independent experiments. Error bars were too small to be visible. The activity of recombinant *E. coli*-derived human ERp57 at higher concentrations was not measured due to the absence of large amount of the protein. As shown in FIG. 19, both recombinant human ERp57 proteins catalyzed the reduction of insulin in slower rate than thioredoxin, in agreement with the results of the previous studies (Hirano et al., 1995; Frickel et al., 2004). Nevertheless, activity of yeast-secreted human ERp57 was slightly but reliably higher than that of *E. coli*-derived protein (note—higher activity of the proteins is represented by the lower position on Y axis in FIG. 19 diagram, as shorter time for insulin precipitation indicates faster catalization of the reaction). This may be explained by the fact that yeast-secreted human ERp57 must undergo thorough protein quality control throughout the yeast secretion pathway, which allows secretion of correctly folded proteins only, meanwhile *E. coli*-synthesized ERp57 is purified by capturing all histidine tag-containing proteins independently of their folding state. In summary, our method for production of native recombinant human ERp57 yields active protein, thus enabling its application in various studies.

Figure 20:
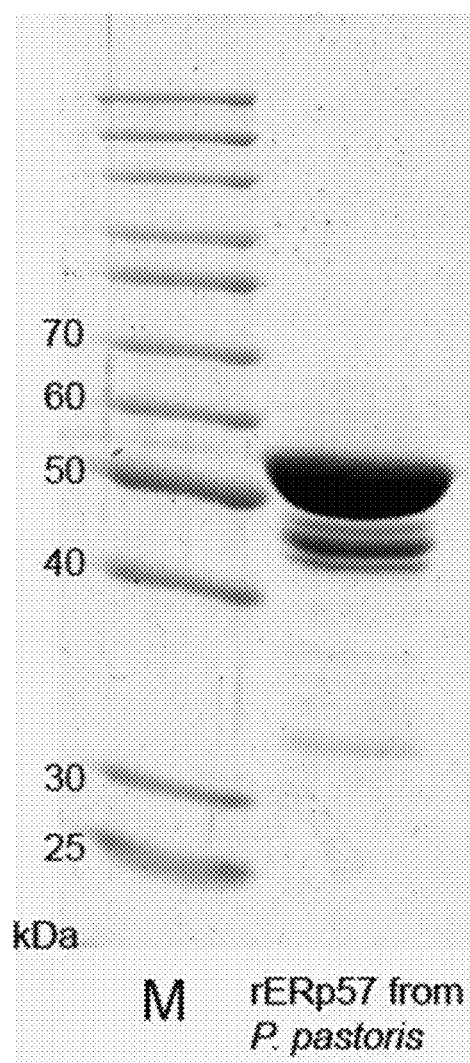
FIG. 20 shows SDS-PAGE of secreted recombinant human ERp57 purified from P. pastoris.

Together with *S. cerevisiae* we have also performed human ERp57 expression experiments in yeast *P. pastoris* system. The whole cDNA of PDIA3 gene was cloned into pPIC3.5K vector under control of AOX1 promoter, similarly as in the cases of expression of human genes encoding BiP and calreticulin proteins. However, in the case of ERp57 the expression under standard conditions recommended by manufacturer (Invitrogen) was less successful as ERp57 secretion level was much lower than that of secretion of this protein in *S. cerevisiae* (not shown). Then we used optimized *P. pastoris* culturing conditions at 20° C. in growing medium containing 1% YNB, 2% peptone, 1% yeast extract, buffered by 100 mM potassium phosphate (pH 6.0) and including 1% glycerol or 1% methanol for generation of yeast biomass or induction of PDIA3 gene expression, respectively. Under these optimised conditions we achieved high-level secretion of ERp57 into the culture medium. A clear human ERp57 protein band was visible in SDS-PAGE after loading of unconcentrated culture medium sample (FIG. 3, panel C lane rERp57). Then the protein was purified from *P. pastoris* culture medium using exactly the same method as for *S. cerevisiae*-expressed ERp57. Purification procedure has yielded ~30 mg of purified human protein from 1 liter of *P. pastoris* culture medium. SDS-PAGE analysis of *P. pastoris*-derived human ERp57 protein is shown in FIG. 20. 5 μg of purified protein was loaded onto SDS-PAA gel lane. N-terminal sequencing by Edman degradation displayed the same N-terminal amino acid sequence $NH_2$—SDVLE for *P. pastoris*-expressed human ERp57. As it is noted above, the same result was obtained for analogue protein expressed in *S. cerevisiae*. Therefore, both yeasts correctly processed and secreted large amounts of native recombinant human ERp57 protein.

This Example provides a simple method for production of native recombinant human ERp57 protein. The exemplified system, using both yeast *S. cerevisiae* and *P. pastoris* cells, allowed production of human thiol-disulfide oxidoreductase ERp57 in eukaryotic endoplasmic reticulum, where the environment is well suited for maturation of such proteins. The disclosed method demonstrated that the native signal of human ERp57 protein was correctly cleaved and drove its secretion outside the yeast cells. Amino acid sequence of secreted native recombinant human ERp57 protein fully corresponded to mature protein from human cells with no yeast derived modifications. Secretion of human ERp57 protein into the yeast medium not only allowed effective simple and cost-effective one-step purification of the protein, but also ensured its higher activity compared to *E. coli* produced ERp57 protein. Yeast was the perfect host for production of human ERp57 protein and also could serve as a convenient model for studying retention of ER luminal proteins in the ER.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

1. Abcam product: GRP78 BiP protein (Active) (ab78432). 2012. http://www.abcam.com/GRP78-BiP-protein-Active-ab78432.html
2. Abcam product: Calreticulin protein (Human) (ab91577). 2012. http://www.abcam.com/Calreticulin-protein-Human-ab91577.html
3. Abcam product: Calreticulin protein (Rabbit) (ab15729). 2013. http://www.abcam.com/calreticul-protein-ab15729.html
4. Abcam product: ERp57 protein (His tag) (ab92937). 2012. http://www.abcam.com/ERp57-protein-His-tag-ab92937.html
5. Andrin C, Corbett E F, Johnson S, Dabrowska M, Campbell I D, Eggleton P, Opas M, Michalak M: Expression and purification of mammalian calreticulin in *Pichia pastoris*. *Protein Expr Purif*. 2000; 20(2):207-15.
6. Antoniou A N, Ford S, Alphey M, Osborne A, Elliott T, Powis S J: The oxidoreductase ERp57 efficiently reduces partially folded in preference to fully folded MHC class I molecules. *EMBO J*. 2002; 21(11):2655-2663.
7. Baksh S, Burns K, Busaan J, Michalak M: Expression and purification of recombinant and native calreticulin. *Protein Expr Purif*. 1992; 3(4):322-31.
8. Barr K A, Hopkins S A, Sreekrishna K: Protocol for efficient secretion of HSA developed from *Pichia pastoris*. *Pharm Eng*. 1992; 12:48-51.
9. Bedard K, Szabo E, Michalak M, Opas M: Cellular functions of endoplasmic reticulum chaperones calreticulin, calnexin, and ERp57. *Int Rev Cytol*. 2005; 245:91-121.
10. Benyair R, Ron E, Lederkremer G Z: Protein quality control, retention, and degradation at the endoplasmic reticulum. *Int Rev Cell Mol Biol*. 2011; 292:197-280.
11. Bernal-Bayard J, Cardenal-Muñoz E, Ramos-Morales F: The *Salmonella* type III secretion effector, *salmonella* leucine-rich repeat protein (SIrP), targets the human chaperone ERdj3. *J Biol Chem*. 2010; 285(21):16360-16368.
12. Blond-Elguindi S, Fourie A M, Sambrook J F, Gething M J: Peptide-dependent stimulation of the ATPase activity of the molecular chaperone BiP is the result of conversion of oligomers to active monomers. *J Biol Chem*. 1993; 268(17):12730-12735.
13. Braakman I, Bulleid N J: Protein folding and modification in the mammalian endoplasmic reticulum. *Annu Rev Biochem*. 2011; 80:71-99.
14. Braakman I, van Anken E: Folding of viral envelope glycoproteins in the endoplasmic reticulum. *Traffic*. 2000; 1 (7):533-9.
15. Capitani M, Sallese M: The KDEL receptor: new functions for an old protein. *FEBS Lett*. 2009; 583:3863-3871.
16. Celli C M, Jaiswal A K: Role of GRP58 in mitomycin C-induced DNA cross-linking. *Cancer Res*. 2003; 63(18):6016-6025.
17. Cereghino J L, Cregg J M: Heterologous protein expression in the methylotrophic yeast *Pichia pastoris*. *FEMS Microbiol Rev*. 2000; 24(1): 45-66.
18. Chakrabarti A, Chen A W, Varner J D: A review of the mammalian unfolded protein response. *Biotechnol Bioeng*. 2011; 108(12):2777-93.
19. Chaput N, De Botton S, Obeid M, Apetoh L, Ghiringhelli F, Panaretakis T, Flament C, Zitvogel L, Kroemer G: Molecular determinants of immunogenic cell death: surface exposure of calreticulin makes the difference. *J Mol Med (Berl)*. 2007; 85(10):1069-76.
20. Charnock-Jones D S, Day K, Smith S K: Cloning, expression and genomic organization of human placental protein disulfide isomerase (previously identified as phospholipase C alpha). *Int J Biochem Cell Biol*. 1996; 28(1):81-89.
21. Čiplys E, Sasnauskas K, Slibinskas R: Overexpression of human calnexin in yeast improves measles surface glycoprotein solubility. *FEMS Yeast Research*. 2011; 11:514-523.
22. Corbett E F, Michalak K M, Oikawa K, Johnson S, Campbell I D, Eggleton P, Kay C, Michalak M: The conformation of calreticulin is influenced by the endoplasmic reticulum luminal environment. *J Biol Chem*. 2000; 275(35):27177-27185.
23. Corrigall V M, Bodman-Smith M D, Fife M S, Canas B, Myers L K, Wooley P, Soh C, Staines N A, Pappin D J, Berlo S E, van Eden W, van Der Zee R, Lanchbury J S, Panayi G S: The human endoplasmic reticulum molecular chaperone BiP is an autoantigen for rheumatoid arthritis 24. Damasceno L M, Huang C J, Batt C A: Protein secretion in *Pichia pastoris* and advances in protein production. *Appl Microbiol Biotechnol.* 2012; 93(1):31-9.
25. Dean N, Pelham H R: Recycling of proteins from the Golgi compartment to the E R in yeast. *J Cell Biol.* 1990; 111(2):369-377.
26. Ferrarese L, Trainotti L, Gattolin S, Casadoro G: Secretion, purification and activity of two recombinant pepper endo-beta-1,4-glucanases expressed in the yeast *Pichia pastoris*. *FEBS Lett.* 1998; 422(1):23-26.
27. Freiden P J, Gaut J R, Hendershot L M: Interconversion of three differentially modified and assembled forms of BiP. *EMBO J.* 1992; 11(1):63-70.
28. Frickel E M, Frei P, Bouvier M, Stafford W F, Helenius A, Glockshuber R, Ellgaard L: ERp57 is a multifunctional thiol-disulfide oxidoreductase. *J Biol Chem.* 2004; 279(18):18277-18287.
29. Gold L I, Eggleton P, Sweetwyne M T, Van Duyn L B, Greives M R, Naylor S M, Michalak M, Murphy-Ullrich J E: Calreticulin: non-endoplasmic reticulum functions in physiology and disease. *FASEB J.* 2010; 24(3):665-83.
30. Gold L I, Rahman M, Blechman K M, Greives M R, Churgin S, Michaels J, Callaghan M J, Cardwell N L, Pollins A C, Michalak M, Siebert J W, Levine J P, Gurtner G C, Nanney L B, Galiano R D, Cadacio C L: Overview of the role for calreticulin in the enhancement of wound healing through multiple biological effects. *J Investig Dermatol Symp Proc.* 2006; 11(1):57-65.
31. Gonzalez-Gronow M, Selim M A, Papalas J, Pizzo S V: GRP78: a multifunctional receptor on the cell surface. *Antioxid Redox Signal.* 2009; 11(9):2299-306.
32. Gorbatyuk M S, Gorbatyuk O S: The Molecular Chaperone GRP78/BiP as a Therapeutic Target for Neurodegenerative Disorders: A Mini Review. *J Genet Syndr Gene Ther.* 2013; 11; 4(2). pii: 128.
33. Greives M R, Samra F, Pavlides S C, Blechman K M, Naylor S M, Woodrell C D, Cadacio C, Levine J P, Bancroft T A, Michalak M, Warren S M, Gold L I: Exogenous calreticulin improves diabetic wound healing. *Wound Repair Regen.* 2012; 20(5):715-730.
34. Groenendyk J, Sreenivasaiah P K, Kim do H, Agellon L B, Michalak M: Biology of endoplasmic reticulum stress in the heart. *Circ Res.* 2010; 107(10):1185-97.
35. Guo J P, Ma Y: High-level expression, purification and characterization of recombinant *Aspergillus oryzae* alkaline protease in *Pichia pastoris*. *Protein Expr Purif.* 2008; 58(2):301-308.
36. Hamilton S R, Gerngross T U: Glycosylation engineering in yeast: the advent of fully humanized yeast. *Curr Opin Biotechnol.* 2007; 18(5):387-92.
37. Hebert D N, Simons J F, Peterson J R, Helenius A: Calnexin, calreticulin, and Bip/Kar2p in protein folding. *Cold Spring Harb Symp Quant Biol.* 1995; 60:405-15.
38. Hetz C, Russelakis-Carneiro M, Wälchli S, Carboni S, Vial-Knecht E, Maundrell K, Castilla J, Soto C: The disulfide isomerase Grp58 is a protective factor against prion neurotoxicity. *J Neurosci.* 2005; 25(11):2793-802.
39. High S, Lecomte F J, Russell S J, Abell B M, Oliver J D: Glycoprotein folding in the endoplasmic reticulum: a tale of three chaperones? *FEBS Lett.* 2000; 476(1-2):38-41.
40. Hirano N, Shibasaki F, Sakai R, Tanaka T, Nishida J, Yazaki Y, Takenawa T, Hirai H: Molecular cloning of the human glucose-regulated protein ERp57/GRP58, a thiol-dependent reductase. Identification of its secretory form and inducible expression by the oncogenic transformation. *Eur J Biochem.* 1995; 234(1):336-342.
41. Hitzeman R A, Leung D W, Perry L J, Kohr W J, Levine H L, Goeddel D V: Secretion of Human Interferons by Yeast. *Science* 1983, 219:620-5.
42. Hitzeman R A, Leung D W: Expression, processing and secretion of heterologous protein by yeast. Genentech, October 1988: U.S. Pat. No. 4,775,622.
43. Højrup P, Roepstorff P, Houen G: Human placental calreticulin characterization of domain structure and post-translational modifications. *Eur J Biochem.* 2001; 268(9): 2558-2565.
44. Hou J, Tyo K E, Liu Z, Petranovic D, Nielsen J: Metabolic engineering of recombinant protein secretion by *Saccharomyces cerevisiae*. *FEMS Yeast Res.* 2012 Apr. 25. doi: 10.1111/j.1567-1364.2012.00810.x. [Epub ahead of print]
45. Houen G, Koch C: Human placental calreticulin: purification, characterization and association with other proteins. *Acta Chem Scand.* 1994; 48(11):905-11.
46. Kassenbrock C K, Kelly R B: Interaction of heavy chain binding protein (BiP/GRP78) with adenine nucleotides. *EMBO J.* 1989; 8(5):1461-1467.
47. Lee A S: GRP78 induction in cancer: therapeutic and prognostic implications. *Cancer Res.* 2007 Apr. 15; 67(8): 3496-9.
48. Li J, Lee A S: Stress induction of GRP78/BiP and its role in cancer. *Curr Mol Med.* 2006; 6(1):45-54.
49. Luo B, Lee A S: The critical roles of endoplasmic reticulum chaperones and unfolded protein response in tumorigenesis and anticancer therapies. *Oncogene.* 2012 Apr. 16. doi: 10.1038/onc.2012.130. [Epub ahead of print]
50. Ma Y, Hendershot L M: E R chaperone functions during normal and stress conditions. *J Chem Neuroanat.* 2004 September; 28(1-2):51-65.
51. Maffei A, Papadopoulos K, Harris P E: MHC class I antigen processing pathways. *Hum Immunol.* 1997; 54(2): 91-103.
52. Malhotra J D, Kaufman R J: The endoplasmic reticulum and the unfolded protein response. *Semin Cell Dev Biol.* 2007; 18(6):716-31.
53. Mattanovich D, Branduardi P, Dato L, Gasser B, Sauer M, Porro D: Recombinant protein production in yeasts. *Methods Mol Biol.* 2012; 824:329-58.
54. Morito D, Nagata K: E R Stress Proteins in Autoimmune and Inflammatory Diseases. *Front Immunol.* 2012; 3:48. Epub 2012 Mar. 15.
55. Nanney L B, Woodrell C D, Greives M R, Cardwell N L, Pollins A C, Bancroft T A, Chesser A, Michalak M, Rahman M, Siebert J W, Gold L I: Calreticulin enhances porcine wound repair by diverse biological effects. *Am J PathoL* 2008; 173(3):610-30.
56. Ni M, Zhang Y, Lee A S: Beyond the endoplasmic reticulum: atypical GRP78 in cell viability, signalling and therapeutic targeting. *Biochem J.* 2011; 434(2):181-8.
57. Nicchitta C V, Reed R C: The immunological properties of endoplasmic reticulum chaperones: a conflict of interest? *Essays Biochem.* 2000; 36:15-25.
58. Obeid M, Tesniere A, Ghiringhelli F, Fimia G M, Apetoh L, Perfettini J L, Castedo M, Mignot G, Panaretakis T, Casares N, Metivier D, Larochette N, van Endert P, Ciccosanti F, Piacentini M, Zitvogel L, Kroemer G: Calreticulin exposure dictates the immunogenicity of cancer cell death. *Nat Med.* 2007; 13(1):54-61.

59. Panayi G S, Corrigall V M: BiP regulates autoimmune inflammation and tissue damage. *Autoimmun Rev.* 2006; 5(2):140-2.
60. Peters L R, Raghavan M: Endoplasmic reticulum calcium depletion impacts chaperone secretion, innate immunity, and phagocytic uptake of cells. *J Immunol.* 2011; 187(2):919-31.
61. Prevatt W D, Sreekrishna K: Expression of human serum albumin in *Pichia pastoris*. Research Technologies Jul. 19, 1994: U.S. Pat. No. 5,330,901.
62. Rokeach L A, Haselby J A, Hoch S O: High-level bacterial expression, purification and characterization of human calreticulin. *Protein Eng.* 1991; 4(8):981-7.
63. Sambrook J, Russell D W: *Molecular cloning, A Laboratory Manual*. third edition. CSHL Press, Cold Spring Harbour, New York, USA; 2001.
64. Sleep D, Belfield G P, Goodey A R: The secretion of human serum albumin from the yeast *Saccharomyces cerevisiae* using five different leader sequences. *Biotechnology (N Y)*. 1990; 8(1):42-46.
65. Spear E, Ng D T: The unfolded protein response: no longer just a special teams player. *Traffic.* 2001; 2(8):515-23.
66. StressMarq product: GRP78 (Recombinant, Human, Native sequence), (SPR-119B). 2012. http://www.stressmarq.com/Products/Proteins/SPR-119B.aspx
67. Turano C, Gaucci E, Grillo C, Chichiarelli S: ERp57/GRP58: a protein with multiple functions. *Cell Mol Biol Lett.* 2011; 16(4):539-63.
68. USBiological product: Recombinant human BIP protein (B1770-01). 2012. http://www.usbio.net/item/B1770-01
69. USBiological product: Recombinant human Calreticulin (C1036-02L1). 2012. http://www.usbio.net/item/C1036-02L1
70. USBiological product: Recombinant human PDIA3 protein (E2291-75E). 2012. http://www.usbio.net/item/E2291-75E
71. Yoo S A, You S, Yoon H J, Kim D H, Kim H S, Lee K, Ahn J H, Hwang D, Lee A S, Kim K J, Park Y J, Cho C S, Kim W U: A novel pathogenic role of the E R chaperone GRP78/BiP in rheumatoid arthritis. *J Exp Med.* 2012 Apr. 9; 209(4):871-86. Epub 2012 Mar. 19.
72. Wearsch P A, Cresswell P: The quality control of MHC class I peptide loading. *Curr Opin Cell Biol.* 2008; 20(6):624-31.
73. Wei J, Hendershot L M: Characterization of the nucleotide binding properties and ATPase activity of recombinant hamster BiP purified from bacteria. *J Biol Chem.* 1995; 270(44):26670-26676.
74. Wemeau M, Kepp O, Tesnière A, Panaretakis T, Flament C, De Botton S, Zitvogel L, Kroemer G, Chaput N: Calreticulin exposure on malignant blasts predicts a cellular anticancer immune response in patients with acute myeloid leukemia. *Cell Death Dis.* 2010; 1:e104.
75. Wessel D, Flügge U I: A method for the quantitative recovery of protein in dilute solution in the presence of detergents and lipids. *Anal Biochem.* 1984; 138(1):141-143.
76. Zhang J X, Braakman I, Matlack K E, Helenius A: Quality control in the secretory pathway: the role of calreticulin, calnexin and BiP in the retention of glycoproteins with C-terminal truncations. *Mol Biol Cell.* 1997; 8(10):1943-54.
77. Zhang Y, Williams D B: Assembly of MHC class I molecules within the endoplasmic reticulum. *Immunol Res.* 2006; 35(1-2):151-62.
78. Zimmermann R, Eyrisch S, Ahmad M, Helms V: Protein translocation across the E R membrane. *Biochimica et Biophysica Acta (BBA)—Biomembranes.* 2011; 1808: 912-924.

What is claimed is:

1. A method for producing a mature human endoplasmic reticulum chaperone protein, wherein the mature human ER chaperone protein is a human ER luminal protein, the method comprising:
   (a) providing a yeast cell transformed with a full-length human chaperone cDNA encoding a polypeptide comprising a native signal sequence and the mature human ER chaperone protein;
   (b) culturing the yeast cell in a culture medium and allowing the yeast cell to express the polypeptide;
   (c) allowing the yeast cell to recognize and correctly process the native signal sequence of the polypeptide to thereby provide the mature human ER chaperone protein;
   (d) allowing the yeast cell to secrete the mature human ER chaperone protein outside the yeast cell and into the culture medium; and
   (e) extracting the mature human ER chaperone protein from the culture medium.

2. The method of claim 1, wherein the yeast is *Saccharomyces cerevisiae*.

3. The method of claim 1, wherein the yeast is *Pichia pastoris*.

4. The method of claim 1, wherein the human endoplasmic reticulum chaperone protein is selected from the group consisting of BiP/GRP78, calreticulin, and ERp57.

5. The method of claim 4, wherein the human endoplasmic reticulum chaperone protein is BiP/GRP78 protein, and the yeast is *Saccharomyces cerevisiae*.

6. The method of claim 4, wherein the human endoplasmic reticulum chaperone protein is BiP/GRP78 protein and the yeast is *Pichia pastoris*.

7. The method of claim 4, wherein the human endoplasmic reticulum protein is calreticulin protein, and the yeast is *Saccharomyces cerevisiae*.

8. The method of claim 4, wherein the human endoplasmic reticulum protein is calreticulin protein and the yeast is *Pichia pastoris*.

9. The method of claim 4, wherein the human endoplasmic reticulum protein is ERp57 protein and the yeast is *Saccharomyces cerevisiae*.

10. The method of claim 4 wherein the human endoplasmic reticulum protein is ERp57 protein and the yeast is *Pichia pastoris*.

* * * * *

UNITED STATES PATENT AND TRADEMARK OFFICE
CERTIFICATE OF CORRECTION

PATENT NO. : 9,796,971 B2
APPLICATION NO. : 14/594485
DATED : October 24, 2017
INVENTOR(S) : Ciplys et al.

It is certified that error appears in the above-identified patent and that said Letters Patent is hereby corrected as shown below:

On the Title Page

Item (72) should be amended to remove inventors Marek MICHALAK and Leslie Ina GOLD.

Signed and Sealed this
Eleventh Day of September, 2018

Andrei Iancu
*Director of the United States Patent and Trademark Office*